(12) United States Patent
Langer et al.

(10) Patent No.: US 6,727,253 B2
(45) Date of Patent: Apr. 27, 2004

(54) TREATMENT OF ACCIDENTAL EXTRAVASATION OF ANTHRACYCLINES

(75) Inventors: Seppo W. Langer, Gentofte (DK); Peter B. Jensen, Farum (DK); Maxwell Sehested, Copenhagen (DK)

(73) Assignee: Antianthra APS, Farum (DK)

( * ) Notice: Subject to any disclaimer, the term of this patent is extended or adjusted under 35 U.S.C. 154(b) by 0 days.

(21) Appl. No.: 09/893,521

(22) Filed: Jun. 29, 2001

(65) Prior Publication Data

US 2002/0099057 A1 Jul. 25, 2002

Related U.S. Application Data

(63) Continuation-in-part of application No. PCT/DK00/00107, filed on Mar. 13, 2000.

(30) Foreign Application Priority Data

Mar. 12, 1999 (DK) ........................ 1999 00355

(51) Int. Cl.⁷ ............................................ A61K 31/495
(52) U.S. Cl. .................................................. 514/252.11
(58) Field of Search .................................... 514/252.11

(56) References Cited

U.S. PATENT DOCUMENTS

| | | | |
|---|---|---|---|
| 4,963,551 A | 10/1990 | Palepu et al. | ................ 514/252 |
| 5,242,901 A | 9/1993 | Speyer et al. | .................. 514/8 |
| 5,620,961 A | 4/1997 | Markovic et al. | ............. 514/23 |

FOREIGN PATENT DOCUMENTS

| | | |
|---|---|---|
| FR | 2758264 | 7/1998 |
| WO | 9307873 | 4/1993 |
| WO | 9321938 | 11/1993 |
| WO | 9323075 | 11/1993 |
| WO | 9725044 | 7/1997 |
| WO | 9841202 | 9/1998 |

OTHER PUBLICATIONS

Andoh, et al., *Catalytic Inhibitors DNA topoisomerase II*, Biochimica et Biophysica Acta, vol. 1400, pp. 155–171, 1998.
Averbuch, et al., *Doxorubicin–Induced Skin Necrosis in the Swine Model: Protection With a Novel Radical Dimer*, Journal of Clinical Oncology, vol. 4, No. 1, pp. 88–94, Jan., 1986.
Banerjee, et al., *Cancer chemotherapy agent–induced perivenous extravasation injuries*, Postgraduate Medical Journal, vol. 63, pp. 5–9, 1987.
Bekerecioğlu, et al., *Prevention of Adriamycin–Induced Skin Necrosis With Various Free Radical Scavengers*, Journal of Surgical Research, vol. 75, pp. 61–65, 1998.
Berger, et al., *Structure and mechanism of DNA topoisomerase II*, Nature, vol. 379, pp. 225–232, Jan. 1996.
Bleicher, et al., *The Delineation of Adriamycin Extravasation Using Fluorescence Microscopy*, Plastic And Reconstructive Surgery, vo. 74, No. 1, pp. 114–116, Jul. 1984.

Brothers, et al., *Experience with Subcutaneous Infusion Ports in Three Hundred Patients*, Surgery, Gynecology & Obstetrics, vol. 166, No. 4, pp. 295–301, Apr. 1988.
Chen. et al., *DNA Topoisomerases: Essential Enzymes and Lethal Targets*, Annu. Rev. Pharmacol. Toxicol., vol. 34, pp. 191–218, 1994.
Dahlstrøm, et al., *Fluorescence Microscopic Demonstration and Demarcation of Doxorubicin Extravasation*, Cancer, vol. 65, No. 8, pp. 1722–1726, Apr. 15, 1990.
Bartkowski–Dodds, et al., *Use of Sodium Bicarbonate as a Means of Ameliorating Doxorubicin–induced Dermal Necrosis in Rats*, Cancer Chemother. Pharmacol., vol. 4, pp. 179–181, 1980.
Disa, et al., *Prevention of Adriamycin–Induced Full–Thickness Skin Loss Using Hyaluronidase Infiltration*, Plastic and Reconstructive Surgery, vol. 101, No. 2, pp. 370–374, Feb. 1993.
Dorr, et al., *Cold Protection and Heat Enhancement of Doxorubicin Skin Toxicity in the Mouse*, Cancer Treatment Reports, vol. 69, No. 4 pp. 431–437, Apr. 1985.
Dorr, et al., *Failure of DMSO and Vitamin E to Prevent Doxorubicin Skin Ulceration in the Mouse*, Cancer Treatment Reports, vol. 67, No. 5, pp. 499–501, May 1983.
Dorr, et al., *Modulation of Experimental Doxorubicin Skin Toxicity by β–Adrenergic Compounds*, Cancer Research, vol. 41, pp. 2428–2431, Jun. 1981.
Dorr, et al., *The Limited Role of Corticosteroids in Ameliorating Experimental Doxorubicin Skin Toxicity in the Mouse*, Cancer Chemother. Pharmacol., vol. 5, pp. 17–20, 1980.
Froelich–Ammon, et al., *Topoisomerase Poisons: Harnessing the Dark Side of Enzyme Mechanism*, The Journal of Biological Chemistry, vol. 270, No. 37, pp. 21429–21432, Sep. 1995.
Hasinoff, *The iron (III) and copper (II) complexes of adriamycin promote the hydrolysis of the cardioprotective agent ICRF–187 ((+)–1,2–bis(3,5–dioxopiperazinyl–1–yl)propane)* Agents And Actions, vol. 29, pp. 374–381, 19990.
Herman, et al., *Biological Properties of ICRF–159 and Related Bis(dioxopiperazine) Compounds*, Advances In Pharmacology And Chemotherapy, vol. 19, pp. 249–290, 1982.
Herman, et al., *Comparison of the Protective Effect of ICRF–187 and Structurally Related Analogues Against Acute Daunorubicin Toxicity in Syrian Golden Hamsters*, Research Communications In Chemical Pathology And Pharmacology, vol. 48, No. 1, pp. 39–55, Apr. 1985.

(List continued on next page.)

Primary Examiner—Phyllis G. Spivack
(74) Attorney, Agent, or Firm—Iver P. Cooper

(57) ABSTRACT

The present invention relates to a method for pharmacological treatment of accidental extravasation of topoisomerase II poisons, such as anthracyclines. In particular, the invention relates to the use of a topo II catalytic inhibitor, such as the bisdioxopiperazine ICRF-187, for the treatment of an accidental extravasation of a topoisomerase II poison. A method for treatment of such extravasation of a topoisomerase poison such as the anthracyclines, daunorubicin, doxorubicin, epirubicin, or idarubicin is disclosed.

31 Claims, 12 Drawing Sheets

OTHER PUBLICATIONS

Ishida, et al., *Inhibition of Intracellular Topoisomerase II by Antitumor Bis(2,6–dioxopiperazine) Derivatives: Mode of Cell Growth Inhibition Distinct from that of Cleavable Complex–forming Type Inhibitors*, Cancer Research, vol. 51, pp. 4904–4916, Sep. 15, 1991.

Jensen, et al., *Targeting the Cytotoxicity of Topoisomerase II–directed Epipodophyllotoxins to Tumor Cells in Acidic Environments*, Cancer Research, vol. 54, pp. 2959–2963, Jun. 1, 1994.

Lossos, *Cutaneous and subcutaneous necrosis following dexrazoxane–CHOP therapy*, Annals of Pharmacotherapy, vol. 33, pp. 253–254, Feb. 1999.

Loth, et al., *Treatment methods for extravasations of chemotherapeutic agents: A comparative study*, The Journal of Hand Surgery, vol. 11A, No. 3, pp. 388–396, May 1996.

Luedke, et al., *Histopathogenesis of Skin and Subcutaneous Injury Induced by Adriamycin*, Plastic And Recontructive Surgery, vol. 63, , No. 4, pp. 463–465, Apr. 1979.

Roca, et al., *Antitumor bisdioxopiperazines inhibit yeast DNA topoisomerase II by trapping the enzyme in the form of a closed protein clamp*, Proc. Natl. Acad. Sci. USA, vol. 91, pp. 1781–1785, Mar. 1994.

Roca, et al., *DNA transport by a type II topoisomerase: Direct evidence for a two–gate mechanism*, Proc. Natl. Acad. Sci. USA, vol. 93, pp. 4057–4062, Apr. 1996.

Roca, et al., *DNA transport by a type II Topoisomerase: Evidence in Favor of Two–Gate Mechanism*, Cell, vol. 77, pp. 609–616, 1994.

Rudolph, et al., *Experiment Skin Necrosis Produced by Adriamycin*, Cancer Treatment Reports, vol. 63, No. 4, pp. 529–537, Apr. 1979.

Sehested, et al., *Chinese Hamster Ovary Cells Resistant to the Topoisomerase II Catalytic Inhibitor IRF–159: A Tyr49Phe Mutation Confers High–Level Resistance to Bisdioxopiperazines*, Cancer Research, vol. 58, pp. 1460–1468, Apr. 1, 1998.

Sehested, et al., *Mapping of DNA Topoisomerase II Poisons (Etoposide, Clerocidin) and Catalytic Inhibitors (Aclarubicin, ICRF–187) to Four Distinct Steps in the Topoisomerase II Catalytic Cycle*, Biochemical Pharmacology, vol. 51, pp. 879–885, 1996.

Soble, et al., *Dose–dependent skin ulcers in mice treated with DNA binding antitumor antibiotics*, Cancer Chemother Pharmacol. vol. 20, pp. 33–36, 1987.

Sonneveld, et al., *Long Persistence of Doxorubicin in Human Skin After Extravasation*, Cancer Treatment Reports, vol. 68, No. 6, pp. 895–896, Jun. 1984.

Sorensen, et al., *Mode of Action of Topoisomerase II–targeting Agents at a Specific DNA Sequence*, J. Mol. Biol., vol. 228, pp. 778–786, 1992.

Sorensen, et al., *pH–Dependent Regulation of Camptothecin–Induced Cytotoxicity and Cleavable Complex Formation by the Antimalarial Agent Chloroquine*, Biochemical Pharmacology, vol. 54, pp. 373–380, 1997.

Tanabe, et al., *Inhibition of Topoisomerase II by Antitumor Agents bis(2,6–dioxopiperazine) Derivatives*, Cancer Research, vol. 51, pp. 4903–4908, 1991.

Von Hoff, et al., *Risk Factors of Doxorubicin–Induced Congestive Heart Failure*, Annals of Internal Medicine, vol. 91, pp. 710–717, 1979.

Von Hoff, et al., *Risk Factors for Development of Daunorubicin Cardiotoxicity*, Cancer Treatment Reports, vol. 65, suppl. 4, pp. 19–23, 1981.

Wessel, et al., *Human Small Cell Lung Cancer NYH Cells Selected for Resistance to the Bisdioxopiperazine Topoisomerase II Catalytic Inhibitor ICRF–187 Demonstrate a Functional R162Q Mutation in the Walker A Consensus ATP Binding Domain of the α Isoform*, Cancer Research, vol. 59, pp. 3443–3450, Jul. 15, 1999.

Langer, et al., *The catalytic topoisomerase II inhibitor dexrazoxane (ICRF–187) markedly reduces tissue damage from extravasation of daunorubicin in mice*, Proceedings of the American Association for Cancer Research, vol. 40, Mar. 1999, Abstract #4500.

The proposed structure and catalytic cycle of topo II entailing cleavage of one DNA segment (G) and passage of another (T). The enzyme is a homodimer consisting of three segments. Topo II poisons act at stages 3-4 when a segment is cleaved. The catalytic inhibitors act either at stage 1 (chloroquine and aclarubicin) or at stage 5 (ICRF-187).

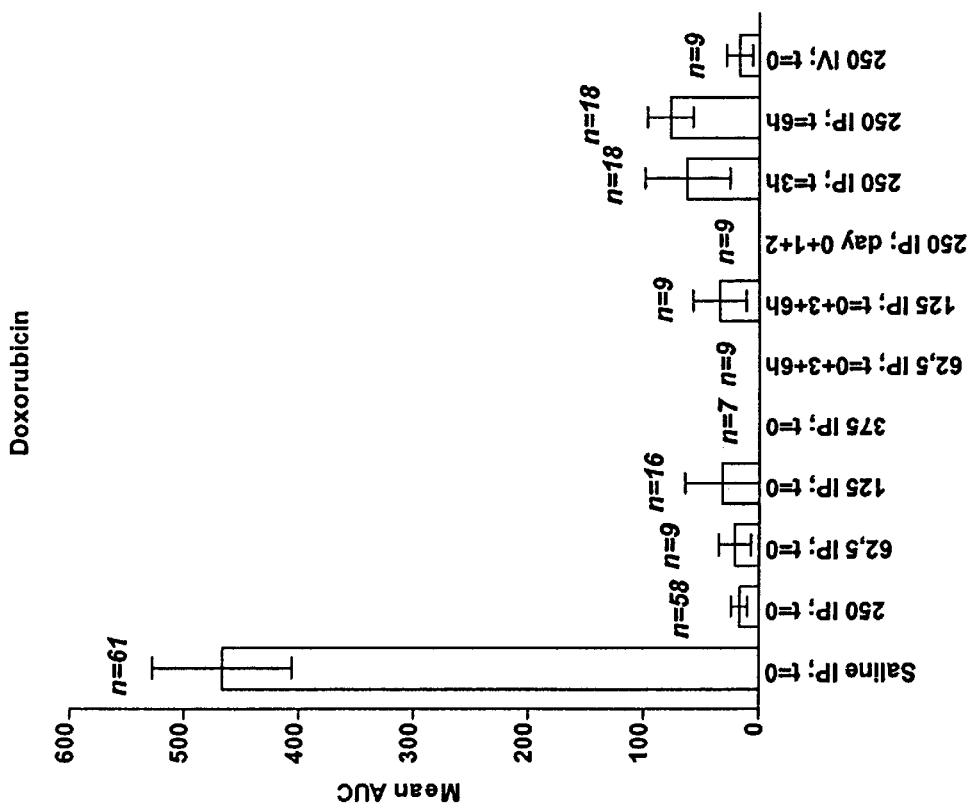

TREATMENT OF ACCIDENTAL EXTRAVASATION OF ANTHRACYCLINES

This is a continuation-in-part of Application No. PCT/DK00/00107, filed Mar. 13, 2000.

The present invention relates to a method and medicament for pharmacological treatment of accidental extravasation of topoisomerase II poisons such as anthracyclines.

In particular, the invention relates to the systemic as well as the local administration of a topo II inhibitor such as the bisdioxopiperazine ICRF-187 in the treatment of accidental extravasation of a topoisomerase II poison such as the anthracyclines daunorubicin, doxorubicin, epirubicin, or idarubicin.

BACKGROUND OF THE INVENTION

Topoisomerase II, topoisomerase II poisons, and topoisomerase II catalytic Inhibitors The topoisomerase II (topo II) enzymes belong to a system of nuclear enzymes involved in the processing of DNA during the cell cycles. In short, they are able to introduce transient cleavage of both strands of the DNA double helix, thereby allowing the passage of another intact DNA double strand through the cleavage. The cleavage time is very short. Drugs acting on topo II are divided into two main categories, topo II poisons and topo II catalytic inhibitors.

The topo II poisons shift the equilibrium of the catalytic cycle towards cleavage, thereby increasing the concentration of the transient protein-associated breaks in the genome (1) (see FIG. 1). That is, they trap the cleavable complexes, which converts the essential topo II enzyme into a lethal one (2).

The topo II catalytic inhibitor is an entirely different group of drugs. They act by interfering with the overall catalytic function, which can be accomplished in at least two ways. One is the inhibition of the initial binding of topo II to DNA as in the case of chloroquine (3) and aclarubicin (4,5). The other is by locking topo II in its closed-clamp step after religation as appears to be the case for the ICRF-187 and its analogues (6–9).

Anthracyclines

The anthracyclines comprise a group of widely used cytotoxic compounds with activity in numerous malignant diseases.

Daunorubicin, the first anthracycline antibiotic to be discovered in the early 1960's, was isolated from streptomyces cultures. Soon hereafter, doxorubicin was extracted and investigated clinically. The two drugs have a wide range of activity against malignant diseases—daunorubicin primarily in the field of haematological malignancies and doxorubicin against solid tumors. Epirubicin is a stereoisomer of doxorubicin with the same indications as but slightly lesser potency and less cardiac toxicity than the parent drug. Idarubicin (4-demethoxydaunorubicin) resembles daunorubicin but lacks a methoxyl group at the C-4 position. It is more lipophilic than the other anthracycline compounds and penetrates the blood-brain barrier more readily.

The mechanism of action of these drugs is not well understood. The antitumor effect is explained by the ability to inhibit the nuclear enzyme DNA topo II. Thus, the anthracyclines are classified as topo II poisons. However, the drugs also interact with other enzymes, e.g. topo I, DNA- and RNA polymerases, and helicases. Furthermore, they are able to intercalate with DNA, a process that may initiate free radical damage. During the intracellular metabolism of the anthracycline, the anthraquinone nucleus is converted to a free radical semiquinone intermediate that might exert local DNA destruction. Moreover, the anthracyclines are capable of chelating iron and forming ternary complexes with DNA. However, the drug concentration required to induce free radical DNA damage is higher than the achievable clinical concentrations. Thus, this mechanism appears to be less important in regard to antitumor effect.

The most pronounced side effects of anthracycline therapy are cardiotoxicity (10,11), hematological toxicity, gastointestinal toxicity, and the extremely severe local toxicity following accidental extravasation (see below).

ICRF-187

The bisdioxopiperazine ICRF-187 (dexrazoxane) is the water-soluble (+) enantiomer of razoxane (ICRF-159). It is a highly specific topo II catalytic inhibitor. A hypothesis has been that ICRF-187, as an analogue of the cation binder EDTA, protects against free radical damage by binding and thus concealing iron from oxygen (12). However, we have recently demonstrated that cells with acquired resistance to ICRF-187 carry mutations in topo II (a subtype of topo II) which are in different sites than those induced by topo II poisons such as daunorubicin and etoposide. We confirmed that these mutations were functional using humanised topo II in yeast (13, 14). Accordingly, our assumptions were correct when we suggested that ICRF-187 was a specific topo II agent. We have demonstrated that it is possible to abolish the cell kill caused by etoposide, daunorubicin, and idarubicin at 2 different steps (See also FIG. 2) in the enzyme's catalytic cycle. Thus, intercalating drugs as chloroquine inhibit the enzyme from reaching its target (3,15,16) and the bisdioxopiperazine ICRF-187 locks the enzyme at a closed clamp step (4,17,18).

ICRF-187 is registered as a cardioprotective agent (Zinecard®, Cardioxane®) against anthracycline induced cardiotoxicity.

Extravasation of Anthracyclines

Accidental extravasation has been estimated to occur in 0.6 to 6% of all patients receiving chemotherapy. Chemotherapeutic agents such as the anthracyclines which bind to DNA are especially prone to cause severe tissue damage on extravasation. The tissue injury may not appear for several days or even weeks and may continue to worsen for months, probably due to drug recycling into adjacent tissue. The local toxicity is characterized by acute pain, erythema, and swelling at the extravasation site and it often progresses to ulceration. Indeed, it has been demonstrated that the anthracyclines, e.g. doxorubicin, can persist in the tissue for at least a month (20). While small ulcerations may on occasion heal, large ulcerations require surgical excision for relief of pain and salvage of underlying tissue. An early surgical approach with extensive debridement of the involved area followed by skin grafting is therefore the treatment of choice (21).

During the last two decades a number of possible treatment modalities have been investigated.

Local cooling with ice lasting from 1 hour to 3 days or longer is a widely used treatment (22), that should be initiated immediately. The use of local injection or topical administration of corticosteroids as an anti-inflammatory treatment has produced contradictory results in animal and human studies (23). Inflammation does not seem to be a part of the pathophysiology and corticosteroids may even worsen the lesions. The effect of local sodium bicarbonate (24) has been investigated in experiments with varying results as have local sodium thiosulphate, hyaluronidase (25), and beta-adrenergics (agonists and antagonists) (26). Experimental treatment and clinical use of topical dimethyl sulfoxide (DMSO) for 2 to 7 days with or without α-tocoferol (vitamin E) (27–29) has indicated beneficial effect in both animal and in uncontrolled clinical studies, at least of DMSO. The results are however not uniform. In one study intraperitoneal (IP) as well as topical treatment with α-tocoferol, *Ginkgo biloba* extract, or pentoxifylline of intradermal (ID) doxorubicin in rats decreased the tissue level of malondialdehyde, thus suggestive of scavenge of free radicals (29). Bi(3,5-dimethyl-5-hydroxymethyl-2-oxomorpholin-3-yl) (DHM3) can react with doxorubicin in vitro to produce an inactive metabolite deoxy-doxorubicin aglycone, and intralesional treatment with DHM3 of ID doxorubicin extravasation in a swine has shown some benefit (30). No confirmative studies have though been published since 1988.

In the almost all animal studies anthracycline has been injected intradermally. It has been argued, that injections beneath the rodent skin muscle layer, panniculus carnosus, tend to cause irregular ulcerative lesions, whereas intradermal injection produces uniform skin necrosis and ulceration (32). However, ID injection of anthracyclines has also been the investigated methods in swine models.

Frozen-section fluorescence of doxorubicin and epirubicin extravasation has been claimed to be an efficient method of detection of residual drug in the tissue, that could serve as a guide to surgical treatment of infiltration (31,33).

The histological changes have been studied in a rabbit model, where the earliest changes included vascular obliteration and necrobiosis of collagen. At no point were inflammatory cells found to play a primary role (34). Small vesicles of unknown etiology have been seen in the necrotic dermis of rats (32). No studies have yet investigated apoptosis.

BRIEF DISCLOSURE OF THE INVENTION

No studies mentioning neither ICRF-187 nor other bisdioxopiperazines nor topo II catalytic inhibitors as a treatment option have been published. Moreover, none of the published studies or reviews has discussed the topo II enzymes as a potential target for an antidote to extravasation of anthracyclines or other topo II poisons. Finally, the vast majority of animal experiments have dealt with local treatment of intradermally extravasated anthracyclines. It is our opinion that subcutaneous administration best resembles the clinical reality. Furthermore, as demonstrated in the examples, the wound area x time (the area under the curve, AUC) is a very reproducible parameter.

The issue of local versus systemic treatment is very important, as use of central venous access devices increases. When multiple infusions are anticipated over a prolonged period, placement of subcutaneous reservoirs with long indwelling lines should be considered. This is often the case in anthracycline therapy. The placement of short-term and long-term indwelling central venous catheters has now become a common surgical procedure performed on cancer patients. However, such devices are not free form leakage, displacement problems, or infectious thrombi. An extravasation incidence of 6.4 percent has been reported (35). Obviously it is difficult to treat local extravasation from centrally located indwelling devices. In such a situation a systemic treatment is far more suitable, but has until now not been available.

LEGENDS TO FIGURES

FIG. 1 shows that the topo II poisons trap the cleavable complexes, which converts the essential topo II enzyme into a lethal one.

FIG. 2 shows the proposed structure and catalytic cycle of topo II entailing cleavage of one DNA segment (G) and passage of another (T). The enzyme is a homodimer consisting of three segments. Topo II poisons act at stages 3–4 when a segment is cleaved. The catalytic inhibitors act either at stage 1 (chloroquine and aclarubicin) or at stage 5 (ICRF-187).

Figure 7:
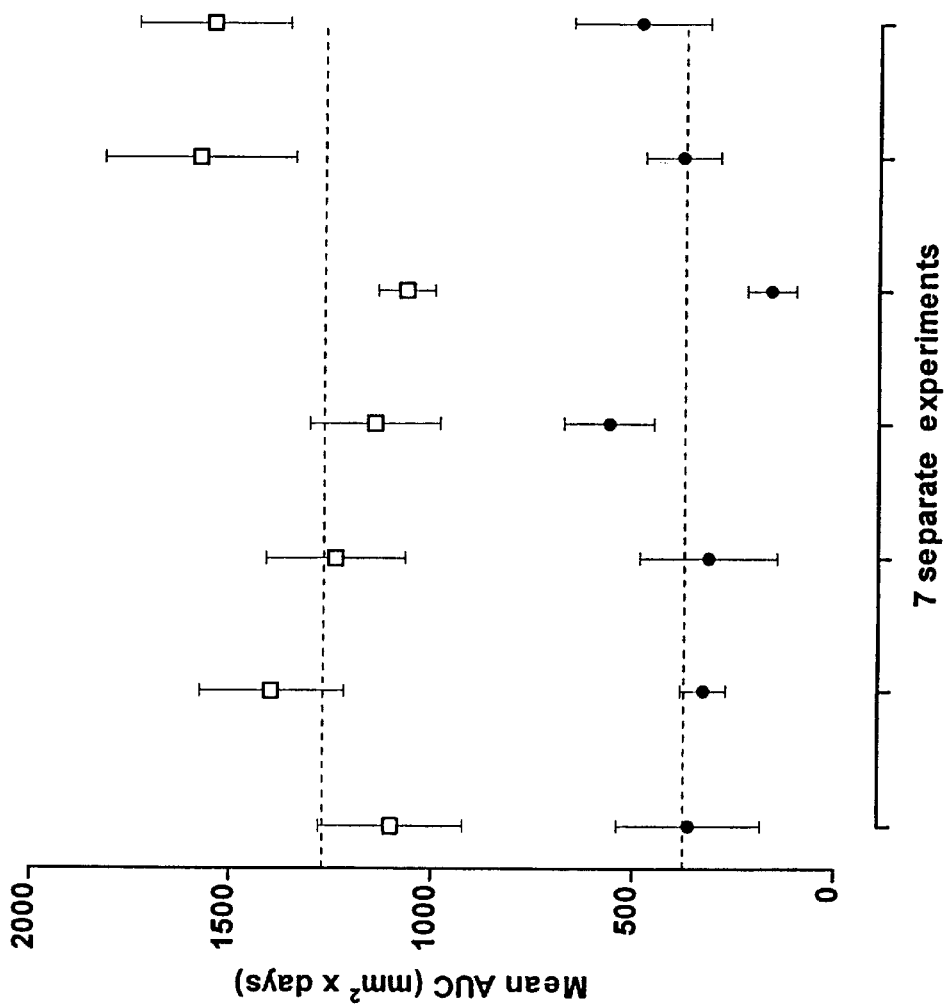
Figure 8A:
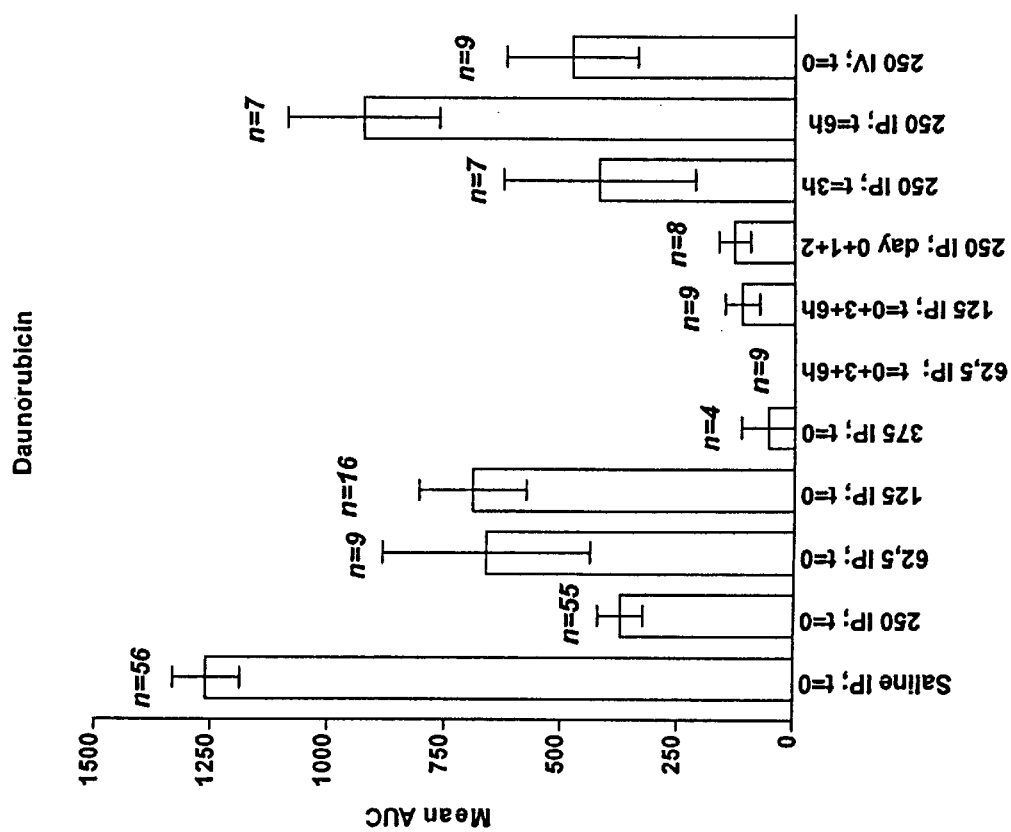

FIG. 7 shows results from Example 11. The mean area under the curve (AUC) from 7 independent experiments with daunorubicin 3 mg/kg SC+/−ICRF-187 250 mg/kg IP at t=0. □=No ICRF-187; •=Plus ICRF-187; - - -=mean; bars= SEM FIG. 8A shows results from Example 11. Mean AUCs of different schedules of ICRF-187 after SC injection of 3 mg/kg daunorubicin.

Figure 8B:
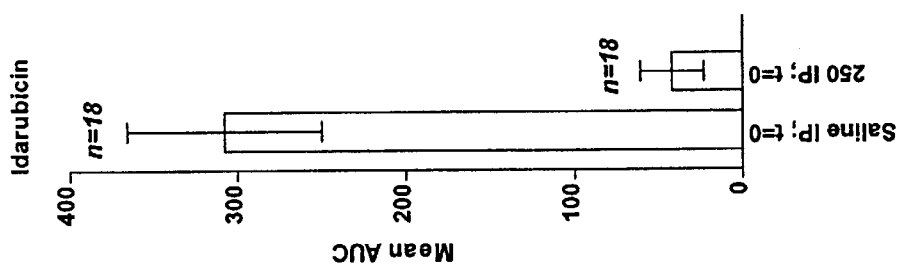

FIG. 8B shows results from Example 11. Mean AUCs of different schedules of ICRF-187 after SC injection of 0.75 mg/kg idarubicin.

FIG. 8C shows results from Example 11. Mean AUCs of different schedules of ICRF-187 after SC injection of 2 or 3 mg/kg doxorubicin.

Figure 9:
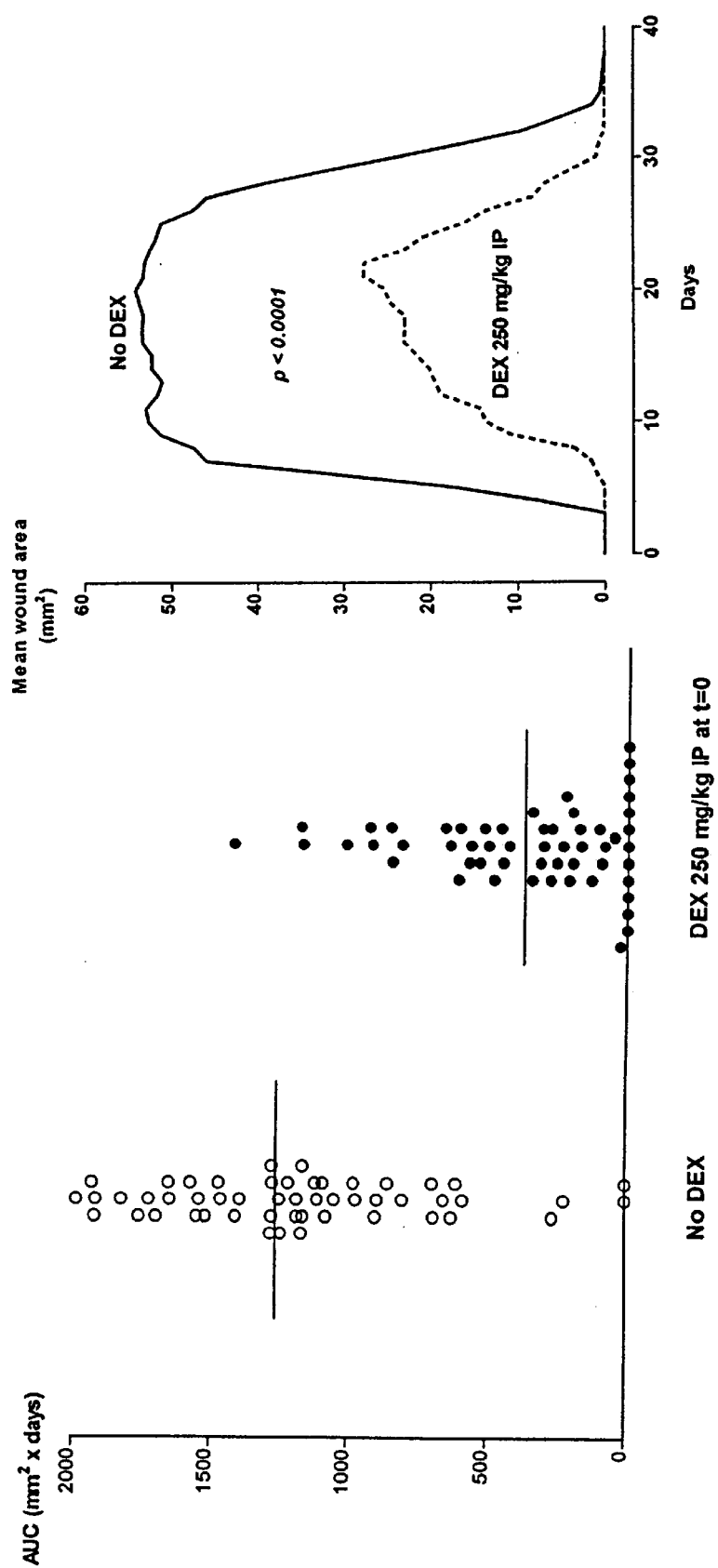

FIG. 9 shows results from Example 11. Left graph: Scatter plot showing the distribution of the AUCs of individual mice after 3 mg/kg daunorubicin SC followed by saline IP (O; n=56) or ICRF-187 250 mg/kg IP at t=0 (•;n=55). Horizontal lines indicate mean AUCs.

Right graph: Mean wound area vs time of the same data as in the left graph

DEX: dexrazoxane=ICRF-187; AUC: Area under the curve.

Figure 10:
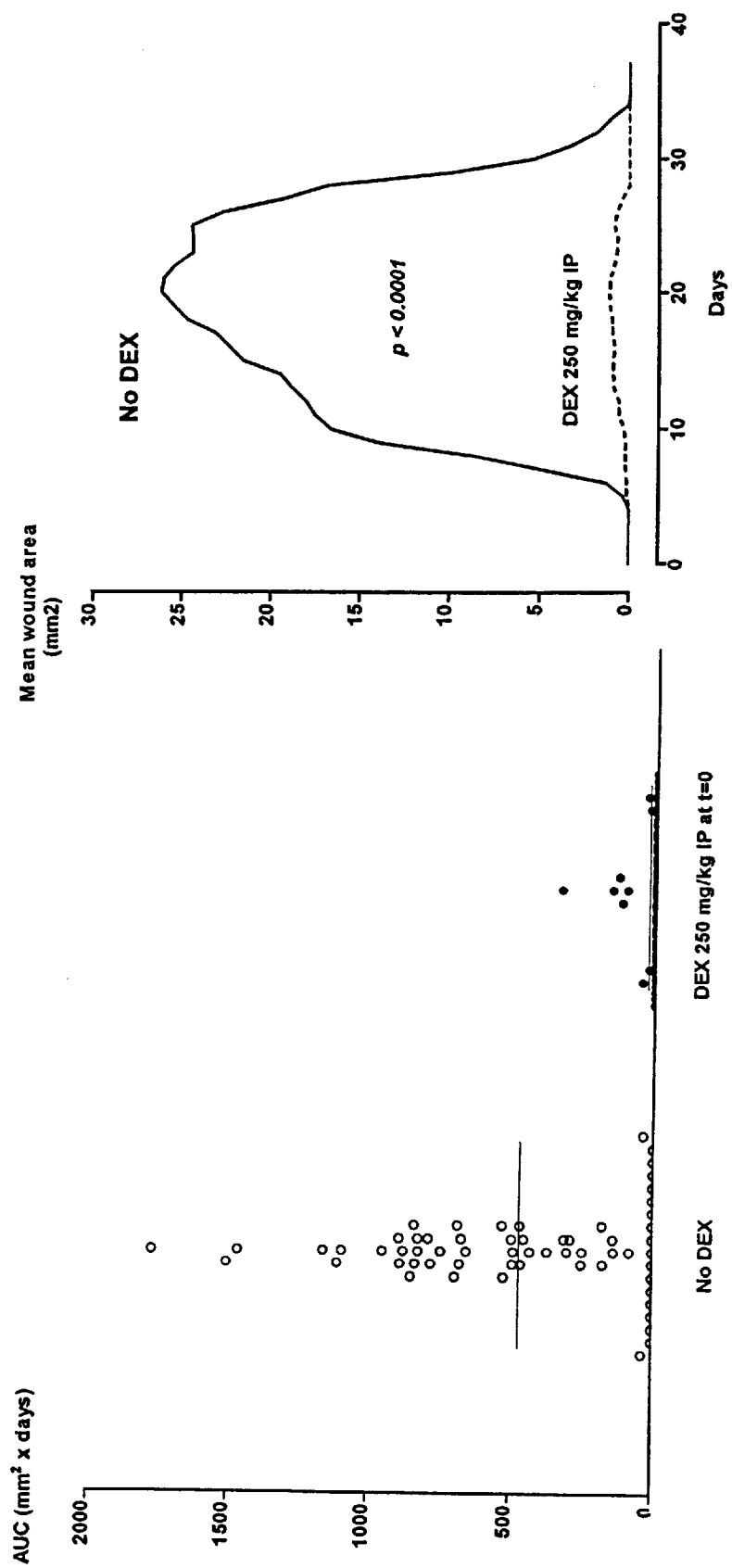

FIG. 10 shows results from Example 11. Left graph: Scatter plot showing the distribution of the AUCs of individual mice after 2 or 3 mg/kg doxorubicin SC followed by saline IP (O; n=56) or ICRF-187 250 mg/kg IP at t=0 (•;n=55). Horizontal lines indicate mean AUCs.

Right graph: Mean wound area vs time of the same data as in the left graph. The difference in AUCs is highly significant.

DEX: dexrazoxane=ICRF-187; AUC: Area under the curve.

DETAILED DISCLOSURE OF THE INVENTION

The present invention provides an effective systemic and/or local treatment of accidental extravasation of topoisomerase poisons such as the anthracyclines daunorubicin, doxorubicin, epirubicin, and idarubicin by use of a topo II catalytic inhibitor such as the bisdioxopiperazine ICRF-187.

In one embodiment the present invention relates to a method for preventing or treating tissue damage due to extravasation of topoisomerase II poisons, including anthracyclines in a patient receiving treatment, normally a systemic treatment, with a topoisomerase II poison. The method comprises administration of a topo II catalytic inhibitor to the patient in need thereof. The signs of a possible extravasation of topoisomerase II poisons is normally immediate pain from the area of extravasation whereby the treatment against the tissue damage may be initiated accordingly. However, the tissue damage may proceed for a long period after the extravasation has occurred so treatment with the topo II catalytic inhibitor may be repeated as often as necessary to secure the optimal inhibition of tissue damage.

The topo II inhibitor according to the invention is preferable selected from the group comprising bisdioxopiperazines; quinolines; aclarubicin; and acridines. The preferred bisdioxopiperazine is ICRF-187 (dexrazoxane). However, the bisdioxopiperazine compounds, to which the present invention relates, includes bis(3,5-dioxopiperazine-1-yl) alkanes having a structure as shown in the general formula I:

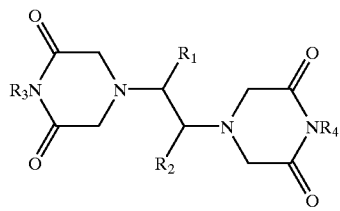

wherein $R^1$ and $R^2$ are independenlty selected from hydrogen and optionally substituted $C_{1-6}$-alkyl, or $R^1$ and $R^2$ together with the intervening atoms form a $C_{3-8}$-carbocyclic ring, and wherein $R^3$ and $R^4$ are selected from hydrogen and optionally substituted $C_{1-6}$-alkyl.

In the present context, the term "$C_{1-6}$-alkyl" designates a linear or branched saturated hydrocarbon group having from one to six carbon atoms, such as methyl, ethyl, n-propyl, isopropyl, cyclopropyl, n-butyl, isobutyl, sec-butyl, tert-butyl, pentyl, isopentyl, neopentyl, hexyl, cyclohexyl.

In the present context, the term "$C_{3-8}$-carbocyclic ring" designates a cyclopropyl, cyclobutyl, cyclopentyl, cyclohexyl, cycloheptyl or cyclooctyl group. It should be understood that when $R^1$ and $R^2$ together with the intervening atoms designates a "$C_{3-8}$-carbocyclic ring", the dioxypiperazine rings may be attached to this carbocyclic ring either trans (E) or cis (Z) relative to the ring. It should also be understood that the carbocyclic ring itself may be substituted with 1–3 groups selected from $C_{1-6}$-alkyl, $C_{1-6}$-alkoxy (=$C_{1-6}$-alkyloxy), etc.

In the present context, the term "optionally substituted" is intended to mean that the alkyl group in question may be 1 to 3 times with one or more groups selected from $C_{1-6}$-alkoxyl, oxo (which may be represented in the tautomeric enol form), carboxyl, amino, hydroxyl, mono- and di($C_{1-6}$-alkyl)amino; carbamoyl, mono- and di($C_{1-6}$-alkyl) aminocarbonyl, halogen (i.e. fluorine, chlorine, bromine and iodine), phenyl or heterocyclyl (e.g. piperidine, piperazine, morpholine, pyrroline, pyrrolidine, pyrazoline and imidazoline).

In a presently preferred embodiment, the meanings of the substituents $R^1$, $R^2$, $R^3$ and $R^4$ include the combinations where $R^1$ and $R^2$ are selected from hydrogen, methyl, ethyl, propyl, isopropyl, methoxymethyl, and ethoxymethyl, and where $R^3$ and $R^4$ are as generally defined above, preferably, however, selected from hydrogen and methyl.

In another preferred embodiment, the meanings of the substituents $R^1$, $R^2$, $R^3$ and $R^4$ include the combinations where $R^1$ and $R^2$ together with the intervening atoms designate a cyclopropyl, cyclobutyl or cyclopentyl ring, and where $R^3$ and $R^4$ are as generally defined above, preferably, however, selected from hydrogen and methyl.

In still another preferred embodiment, the meanings of the substituents $R^1$, $R^2$, $R^3$ and $R^4$ include the combinations where $R^3$ and $R^4$ are selected from hydrogen, methyl and methyl substituted with heterocyclyl, e.g. piperidine, piperazine, morpholine, pyrroline, pyrrolidine, pyrazoline and imidazoline, and $R^1$ and $R^2$ are as generally defined above, preferably, however, selected from hydrogen, methyl, ethyl, propyl, isopropyl, methoxymethyl, and ethoxymethyl, in particular methyl.

In still another preferred embodiment, the meanings of the substituents $R^1$, $R^2$, $R^3$ and $R^4$ include the combinations where $R^1$ and $R^2$ are selected from hydrogen, methyl, ethyl, propyl, isopropyl, methoxymethyl, and ethoxymethyl, and where $R^3$ and $R^4$ are hydrogen.

It should be understood that the substituents $R^1$ and $R^2$ may give rise to optically active forms (i.e. (S) and (R) forms) or racemic mixtures of such forms.

Particularly preferred combinations where $R^3$ and $R^4$ are hydrogen are those where $R^1$=$R^2$=hydrogen, methyl (meso), ethyl (meso), those where $R^1$=hydrogen and $R^2$=methyl (racemic, (S)-(+) (dexrazoxane) or (R)-(−) (levrazoxane), preferably (S)-(+)) and ethyl, and those where $R^1$=methyl and $R^2$=ethyl, propyl, isopropyl and methoxymethyl, the latter in erythro or threo form, preferably erythro.

The administration of the topo II catalytic inhibitor may be by local administration to the tissue affected by the extravasation of the topoisomerase II poison. This includes injection into the area, applying the inhibitor by or with any form of implant, in a dressing, by spraying on any other suitable way. The local treatment may be the sole treatment or a supplemental treatment to a systemic treatment. Local treatment is of special advantage where the extravasation is located in a body cavity such as in the pleura.

In a preferred embodiment, the administration of the topo II catalytic inhibitor is by systemic administration to the tissue affected by the extravasation of the topoisomerase II poison. It is an very important aspect of the invention that the tissue damage may be prevented or treated by a systemic administration as the systemic treatment secure that the inhibitor reach the location of the tissue damage.

It is clear that the administration of the inhibitor will normally be when the extravasation is a reality or it is believed that it has happen. However, in certain circumstances it might be preferred to initiate a prophylactic treatment. This may be the situation where the patient has suffered from extravasation in a earlier treatment with the topo II poison or there is a certain risk of extravasation, e.g. where the patient has very vulnerable veins which is very often the case in patients receiving chemotherapy.

In a preferred embodiment, the topo II catalytic inhibitor is administered after the treatment with the topoisomerase II poison. In a more preferred embodiment, the inhibitor is administered after treatment with the topoisomerase II poison and as long as the tissue stills contains topoisomerase II poison or its active metabolites. In such cases the treatment with the inhibitor may be performed with an interval dependent on the location and degree of the tissue damage. The person skilled in the art will based on the present information be able to suggest a relevant specific treatment procedure based in the individual situation as the main problem is to secure that the inhibitor is present in the relevant area as long as the poison is still active in said tissue area.

The topoisomerase II poisons which may give rise to tissue damage and which may be treated according to the present invention include etoposide, etoposide phosphate, teniposide, daunorubicin, doxorubicin, idarubicin, epirubicin, mitoxantrone, m-AMSA and anthracycline. Moreover, any topoisomerase II poison that inhibits the religation step of the nuclear enzyme topoisomerase II step where the enzyme has created a cleavable complex in DNA is within the scope of the present invention.

In general, there is no reason to administer the inhibitor very long before the poison and it is therefore most preferred to administer the inhibitor substantially concomitantly with the administration of the topoisomerase II poison when a prophylactic treatment is desired.

When the topo II catalytic inhibitor is administered after the administration of the topoisomerase II poison, it should generally be within a period of 3 weeks after the administration of the topo II poison, such as within 2 weeks, preferable within 1 week after, more preferred within 5 days after, even more preferred within 3 days after, still more preferred within 1 day after the administration of the topoisomerase II poison. The 3-week period may illustrate a situation where the poisons or its metabolites are still active in the patient.

In general, the topo II catalytic inhibitor should be administered in the period within 18 hours after the administration of the topo II poison, such as within 12 hours, preferable within 6 hours after, more preferred within 4 hours after, even more preferred within 2 hours after, still more preferred within 1 hour after, and most preferred just after the administration of the topoisomerase II poison to prevent the development of tissue damage from an extravasation. However, for other reasons it may be most convenient to supervise whether any extravasation is present and treat the patient with the inhibitor as soon as possible. Accordingly, in a further aspect, the method according to the invention relates to a situation wherein the topo II catalytic inhibitor is administered upon recognition or suspicion of extravasation of the topoisomerase II poison.

In a preferred embodiment, the topo II catalytic inhibitor is administered with at least 2 repeated dosages, such as at least 3 repeated dosages. Such repeated dosages may be identical of represent a gradually decrease in dosage. It is preferred that the repeated dosages are administered with an interval of 1 to 3 days from the first dosage, preferable with an interval of 2 days, more preferred with an interval of 1 day. However minor intervals of less than 24 hours such as intervals of the most of 18 hours, more preferred at the most 6 hours, such as with intervals of about 3 hours from the first dosage of the II catalytic inhibitor has shown surprising results. The intervals do not have to be identical in that a treatment with increasing intervals may be very advantageous. The skilled person will be able to estimate a sort of "saturation" with relative high dosages or with dosages of minor intervals followed by increasing intervals between the administration of the topo II catalytic inhibitor.

The topo II catalytic inhibitor should be administered within 12 hours, preferable within 6 hours upon recognition or suspicion of extravasation of the topoisomerase II poison. It should be noted that the administration may be performed as a routine in order to prevent damage from a possible extravasation.

In a preferred embodiment, the topo II catalytic inhibitor is a bisdioxopiperazine and the topoisomerase II poison is anthracycline. At present, anthracycline is responsible for the worst cases of tissue damage. Accordingly, the method wherein the anthracycline is selected from daunorubicin, doxorubicin, idarubicin, and epirubicin are very important aspects of the invention.

The topo II inhibitor according to the invention may be a bisdioxopiperazine having the formula stated above and the preferred bisdioxopiperazine is ICRF-187 (dexrazoxane).

Due to the specific circumstances of the present invention it is very difficult to state the exact dosage of the inhibitor. However, with respect to ICRF-187, concentrations and dosages for use of the drug is known from other medical indications and such dosages may be used in the methods according to the present invention. In other cases, the skilled person will be able to suggest relevant dosages, inter alia by administering increasing dosages matching the estimated volume of extravasation of the poison. In general, the risk of tissue damage will increase the risk of side effect from the inhibitor. The purpose with the method according to the present invention is to administer the topo II inhibitor in an amount sufficient to be present in the tissue to be prevented from or treated for tissue damage. As appears from the examples succesful treament has been performed with a repeated dosage between 1000 to 500 mg/kg to a female patient. Accordingly, a repeated dosage of from 100 to 5000 mg/kg may be used according to the present invention. The exact dosage is depending on whether a single dosage or 3 or more repeated dosages is preferred in the specific situation. As indicated in the experiments with mice and swines much smaller dosages of 25 mg/kg in repeated dosages results in a very good effect. Accordingly, similar dosages are within the scope of the present invention.

In a still further aspect, the invention relates to use of a topo II catalytic inhibitor for the preparation of a medicament for treating or preventing tissue damage due to extravasation of a topoisomerase poison in a patient receiving a treatment, such as a systemic treatment with the topoisomerase poison. Accordingly, the invention relates to use of a topo II catalytic inhibitor for the preparation of a medicament for use in any of the methods described herein.

In the present context "treatment with the topoisomerase poison" means an ongoing treatment (e.g. a patient receiving a specific treatment regimen) or a patient who has been treated.

The present invention also relates to a pharmaceutical kit for for preventing or treating tissue damage due to extravasation of a topoisomerase II poisons, including anthracyclines in a patient receiving systemic treatment with the drug, said kit comprising a) a dosage unit of a topoisomerase II poison and optionally a pharmaceutically acceptable carrier, and b) a dosage unit of a topo II catalytic inhibitor and optionally a pharmaceutically acceptable carrier suitable for either local or intravenous administration, and optionally c) a description for providing the topo II catalytic inhibitor to the patient in case extravasation In a preferred embodiment, the present invention relates to a pharmaceutical kit for for preventing or treating tissue damage due to extravasation of anthracyclines in a patient receiving systemic treatment with anthracyclines, said kit comprising a) a dosage unit of an anthracycline and optionally a pharmaceutically acceptable carrier for intravenous administration, and b) a dosage unit of a bisdioxopiperazine and optionally a pharmaceutically acceptable carrier suitable for either local or intravenous administration, and optionally c) a description for providing the topo II catalytic inhibiting bisdioxopiperazine to the patient so that the bisdioxopiperazine is administered in case extravasation.

The kit may include any relevant solvents for the active ingredients and a description for local and/or systemic use of the inhibitor.

In a preferred embodiment, the kit only comprises any of the topo II catalytic inhibitors mentioned herein without the topo II poison.

The kit is preferable performed as an emergency kit which should be available immediately upon a possible extravasation.

The invention is further illustrated by the following examples.

EXAMPLES

Materials and Methods

General Remarks

The experiments were conducted at the Laboratory of Experimental Medical Oncology at the Finsen and Laboratory Centres at the National University Hospital (Rigshospitalet), Copenhagen, Denmark. Inventor #1 and 2 are licensed (Ministry of Justice) to perform experiments on live animals, and thus are bound by the 86/609/EEC (60) and CE (61) conventions.

Mice

Female B6D2F1 hybrid mice were obtained from M&B A/S, Denmark, and kept in a controlled environment with ad libitum access to water and food. All mice went through a pre-experiment acclimatisation period of at least one week. The weight range was 19–21 g at the start of the experiments.

Drugs

The following commercially available drugs were used:
- ICRF-187 hydrochloride (Cardioxane®, Chiron)
- Doxorubicin hydrochloride (Doxorubicin "Paranova"®, Pharmacia)
- Daunorubicin hydrochloride (Cerubidin®, Rhône-Poulenc Rorer)
- Idarubicin hydrochloride (Zavedos®, Pharmacia & Upjohn)
- Epirubicin hydrochloride (Farmorubicin®, Pharmacia & Upjohn)
- Fentanyl-fluanisone (Hypnorm®, Janssen)
- Midazolam (Dormicum®, Roche)

Anesthesia

In all experiments we used a standard solution containing 1 part fentanyl-fluanisone, 1 part midazolam, and 2 parts isotonic saline in an IP dose of 0.1 ml/10 g (62).

Injection Technique

Hair was removed with an electrical shaving device.

Subcutaneous deposition of the anthracycline drug was carried out using a Hamilton® syringe with a 0.05 ml fixed volume deposit and a 27G×¾" needle. The injection site was approximately 1 cm above the root of the tail following retraction of the loose dorsal skin.

ICRF-187 was injected intraperitoneally in a volume of approximately 0.2 ml with a 27G×¾" needle.

When administered intralesionally, ICRF-187 was injected via a separate skin puncture immediately after the anthracycline in a volume of 0.05 ml using a fixed dose deposit Hamilton® syringe.

Identification

Each mouse was ear marked for individual identification.

Observation

Daily measurements were carried out of the two longest perpendicular wound diameters with a ruler. A wound was defined as a tissue lesion of at least 2 mm². Healing was defined as complete regrowth of hair in a wound area. The mice were euthanized after healing of all wounds.

Data Handling and Statistical Methods

Wound size was calculated as the product of the two longest perpendicular diameters in mm. The wound area times duration, i.e. the area under the curve (AUC) was calculated for individual mice. The data sheets presented in the following sections contain the mean AUCs. AUCs, time to wounds, and duration of wounds were compared using the Mann-Whitney test. Fischers exact t-test was used to compare the ulcer rates.

Abbreviations

The following abbreviations are used:

- AUC=area under the curve
- $TTW_W$=time to wound; non-wounded mice excluded
- $DW_W$=duration of wound; non-wounded mice excluded
- $N_W/N_G$=ulcer rate
- SEM=standard error of the mean
- IP=intraperitoneal
- SC=subcutaneous
- IL=intralesional
- IV=intravenous

Example 1

Experiments with Doxorubicin

In Example 1 the effect of different concentrations of ICRF-187 administered IP at t=0, i.e. simultaneously with doxorubicin was investigated. The concentration of doxorubicin was 2 mg/kg, and the volume as previously stated. The control group received saline IP. Twenty-seven mice were used.

The results are depicted in the data sheet for Example 1. Treatment with ICRF-187 125 mg/kg IP resulted in a 91% reduction in AUC from 543 to 48 mm²×days (p<0.05). Increment of the ICRF-187 concentration to 250 and 375 mg/kg resulted in complete prevention of wounds. The ulcer rates were reduced from 86% to 14%, 0%, and 0%, respectively. Due to the small number of wounds in the ICRF-187 treated groups statistical comparisons of changes in the TTWs and DWs are not meaningful. There were no treatment-related deaths.

Data sheet for Example 1

| Group | Treatment | $N_w/N_G$ | Mean AUC (mm² × days) | Mean $TTW_w$ ± SEM (days) | Mean $DW_w$ ± SEM (days) |
|---|---|---|---|---|---|
| 1 | Doxorubicin 2 mg/kg sc + Saline IP | 6/7 86% | 543 | 8.0 ± 0.3 | 24.7 ± 0.5 |
| 2 | Doxorubicin 2 mg/kg sc + ICRF-187 125 mg/kg IP | 1/7 14% | 48 | 9 | 20 |
| 3 | Doxorubicin 2 mg/kg sc + ICRF-187 250 mg/kg IP | 0/6 0% | 0 | — | — |
| 4 | Doxorubicin 2 mg/kg sc + ICRF-187 375 mg/kg IP | 0/7 0% | 0 | — | — |

Example 2

Timing of ICRF-187

The timing of ICRF-187 was investigated in 36 mice. As in Example 1 the concentration of doxorubicin was 2 mg/kg, and saline served as control. ICRF-187 was administered IP in a concentration of 250 mg/kg simultaneously, 3 hours after, or 6 hours after doxorubicin, respectively. The results are depicted in data sheet #2:

Data sheet for Example 2

| Group | Treatment | $N_w/N_G$ | Mean AUC ($mm^2$ × days) | Mean $TTW_w$ ± SEM (days) | Mean $DW_w$ ± SEM (days) |
|---|---|---|---|---|---|
| 1 | Doxorubicin 2 mg/kg sc + Saline IP | 8/9 | 454 | 7.5 ± 1.5 | 23.3 ± 1.8 |
| 2 | Doxorubicin 2 mg/kg sc + ICRF-187 250 mg/kg IP | 5/9 | 45 | 8.6 ± 1.8 | 17.0 ± 2.3 |
| 3 | Doxorubicin 2 mg/kg sc + ICRF-187 250 mg/kg IP 3 hours after doxorubicin | 4/9 | 52 | 6.0 ± 1.1 | 18.5 ± 1.8 |
| 4 | Doxorubicin 2 mg/kg sc + ICRF-187 250 mg/kg IP 6 hours after doxorubicin | 6/9 | 81 | 6.2 ± 1.8 | 19.7 ± 0.4 |

Figure 1:
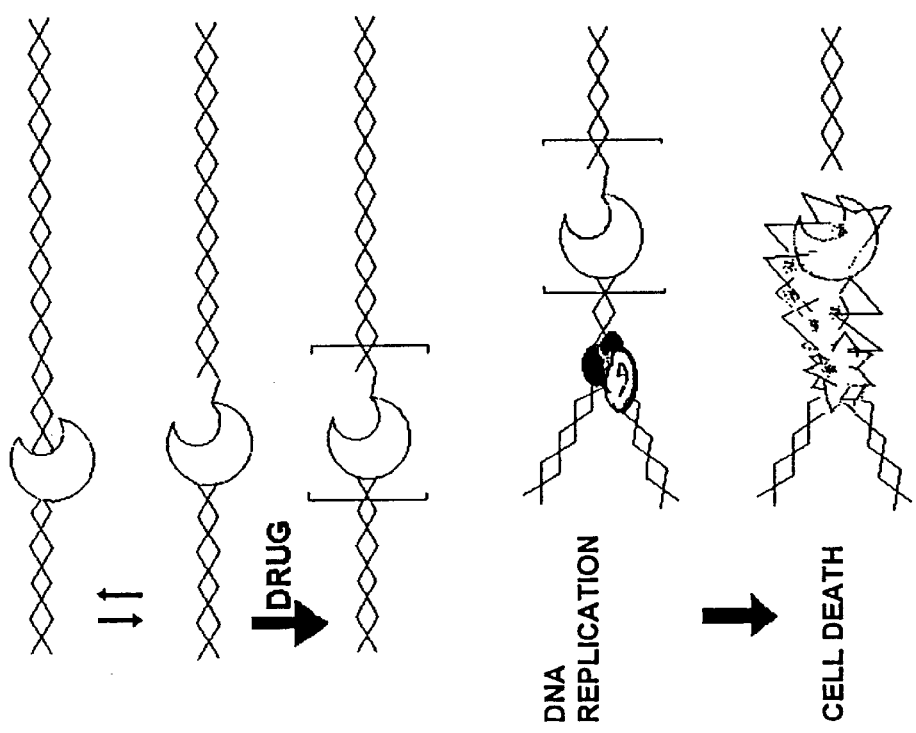
Figure 2:
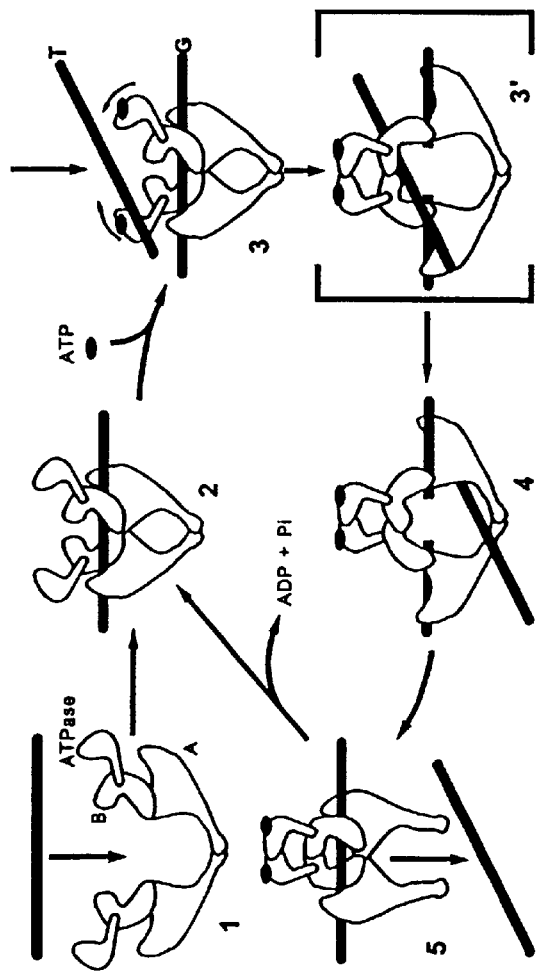
Figure 3:
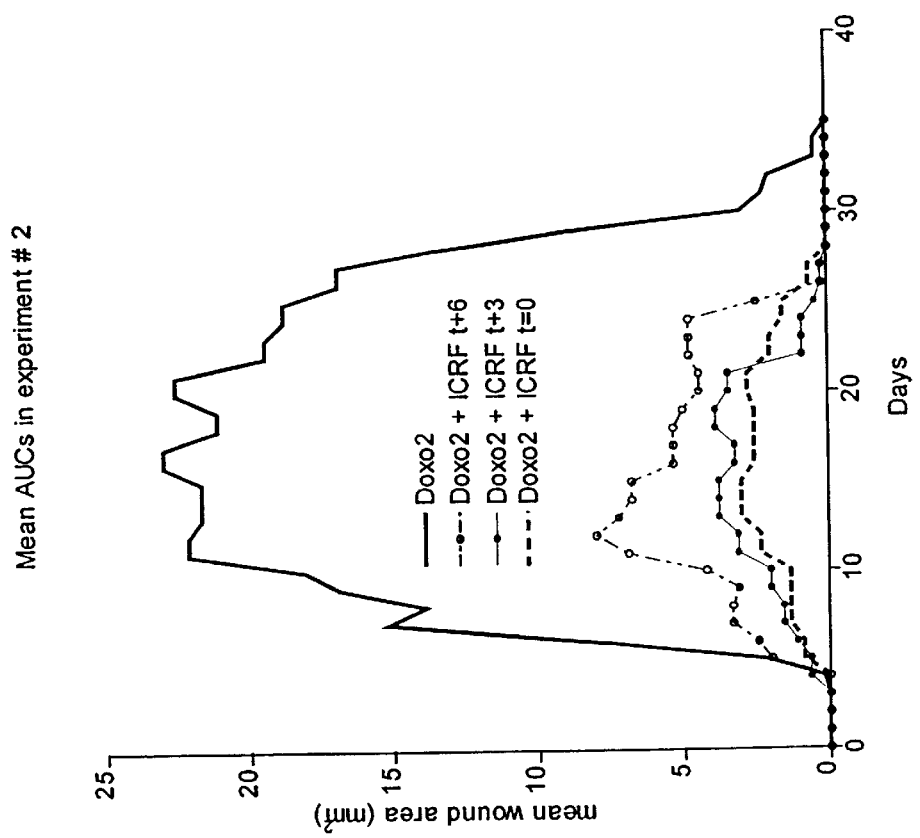
FIG. 3 shows the results from Example 2

Treatment with ICRF-187 resulted in 82–92% reductions in AUCs from 458 to 45, 52, and 81 $mm^2$×days respectively. There was a statistically non-significant trend towards lesser reduction in AUC, when treatment was administered 6 hours after doxorubicin as compared to simultaneous administration. The time to wound and the wound duration were not different. There were no treatment-related deaths. The mean AUCs are shown graphically in FIG. 3.

Overall, treatment with ICRF-187 at t=0 in Example 1 and 2 reduced the ulcer rates from $^{14}/_{16}$ to $^{6}/_{29}$, i.e. from 88% to 21% ($p<0.05$).

Example 3
Experiments with Daunorubicin

The effect of various doses of ICRF-187 was investigated in Example 3. Saline served as a control, which yielded an AUC of 764 $mm^2$×days. Co-treatment with ICRF-187 in a dose of 250 mg/kg and 375 mg/kg resulted in reductions of the AUC with 48% and 93%, respectively ($p<0.05$). The ulcer rates were reduced from 87% to 83 and 25%. There was a conflicting result in the prolongation of the duration of wound in group 2. Otherwise, statistical analysis of the characteristics of the few wounds is not meaningful.

Data sheet for Example 3

| Gr. | Treatment | $N_w/N_G$ | Mean AUC ($mm^2$ × days) | Mean $TTW_w$ ± SEM (days) | Mean $DW_w$ ± SEM (days) |
|---|---|---|---|---|---|
| 1 | Daunorubicin 3 mg/kg sc + Saline IP | 6/7 86% | 764 | 4.8 ± 0.4 | 29.8 ± 0.5 |
| 2 | Daunorubicin 3 mg/kg sc + ICRF-187 250 mg/kg IP | 5/6 83% | 395 | 7.8 ± 1.1 | 29.2 ± 1.1 |
| 3 | Daunorubicin 3 mg/kg sc + ICRF-187 375 mg/kg IP | 1/4 25% | 57 | 4.0 ± 0.0 | 27.0 ± 0.0 |

There were no treatment-related deaths.

Example 4

Comparison of Two Concentrations of sc Daunorubicin

Comparison of two concentrations of sc daunorubicin were compared with and without simultaneous treatment with ICRF-187 250 mg/kg. The results are shown in data sheet for Example 4:

Data sheet for Example 4

| Gr. | Treatment | $N_w/N_G$ | Mean AUC ($mm^2$ × days) | Mean $TTW_w$ ± SEM (days) | Mean $DW_w$ ± SEM (days) |
|---|---|---|---|---|---|
| 1 | Daunorubicin 1 mg/kg sc + Saline IP | 6/7 86% | 365 | 7.3 ± 1.6 | 25.5 ± 1.1 |
| 2 | Daunorubicin 1 mg/kg sc + ICRF-187 250 mg/kg IP | 0/7 0% | 0 | — | — |
| 3 | Daunorubicin 3 mg/kg sc + Saline IP | 6/6 100% | 1240 | 4.8 ± 0.3 | 29.0 ± 0.9 |
| 4 | Daunorubicin 3 mg/kg sc + ICRF-187 250 mg/kg IP | 3/7 43% | 313 | 12.0 ± 3.5 | 14.0 ± 1.5 |

Figure 4:
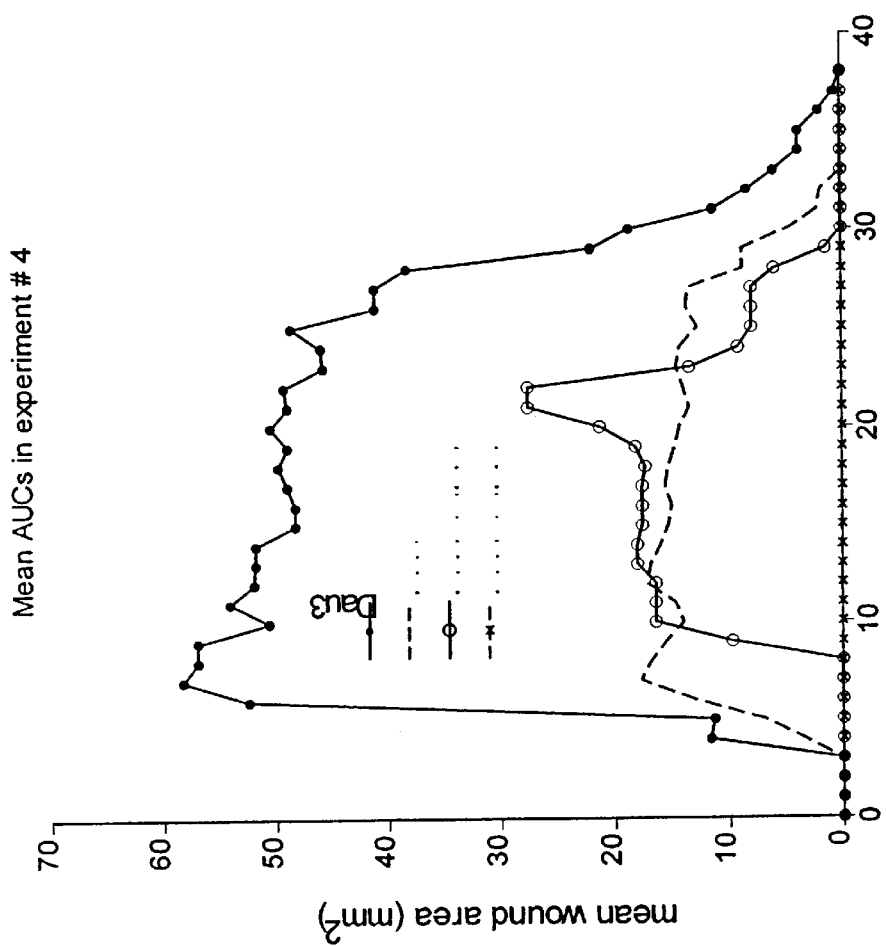
FIG. 4 shows the results from Example 4

The mean AUCs are shown in FIG. 4.

Administration of ICRF-187 resulted in reductions in AUC of 100% and 75% in the low and high dose group, respectively ($p<0.05$). Similarly, the dose dependent difference between AUC in the two control groups (1 and 3) was statistically significant, as were the effects of ICRF-187 on the mean duration of wounds in group 1 vs 2 and 3 vs 4, respectively. The reduction in the ulcer rates in the groups receiving daunorubicin 1 mg/kg was likewise statistically significant, whereas the same trend was observed in the 3 mg/kg-group. This was though not significant.

Example 5

Repetition of Experiment with Larger Groups

The experiments was repeated with larger group sizes in Example 5, where 36 mice were used. As shown in data sheet for Example 5, there was a reduction in the ulcer rates between mice not receiving and those receiving treatment with ICRF-187. Furthermore, ICRF-187 reduced (p<0.05) the AUCs with 73% and 83% in the 1 mg/kg and 3 mg/kg groups, respectively. Moreover, the difference in AUC, the TTW, and the DW between the two controls was statistically significant. There was a trend towards shorter DW and longer TTW between the two low dose groups, which however not was statistically significant. In the groups receiving 3 mg/kg the differences were significant.

Data sheet for Example 5

| Gr. | Treatment | $N_w/N_G$ | Mean AUC ($mm^2$ × days) | Mean $TTW_w$ ± SEM (days) | Mean $DW_w$ ± SEM (days) |
|---|---|---|---|---|---|
| 1 | Daunorubicin 1 mg/kg sc + Saline IP | 8/9 89% | 184 | 8.5 ± 0.7 | 20.5 ± 1.3 |
| 2 | Daunorubicin 1 mg/kg sc + ICRF-187 250 mg/kg IP | 2/9 22% | 50 | 10.5 ± 3.5 | 16.0 ± 4.0 |
| 3 | Daunorubicin 3 mg/kg sc + Saline IP | 9/9 100% | 955 | 5.1 ± 0.2 | 25.7 ± 0.7 |
| 4 | Daunorubicin 3 mg/kg sc + ICRF-187 250 mg/kg IP | 7/9 78% | 158 | 9.9 ± 1.8 | 13.7 ± 1.7 |

Group to group comparison of Example 4 and 5 showed no statistically significant differences between the similar treatments, i.e. it was possible to obtain the same results in the two examples. Thus, the cumulated data from the two experiments reinforced the statistical power of the differences in AUC, TTW and DW between ICRF-treated and non-treated groups and between low and high dose treatment.

Example 6

The Effect of Different Timing of ICRF-187 Administration

Figure 5:
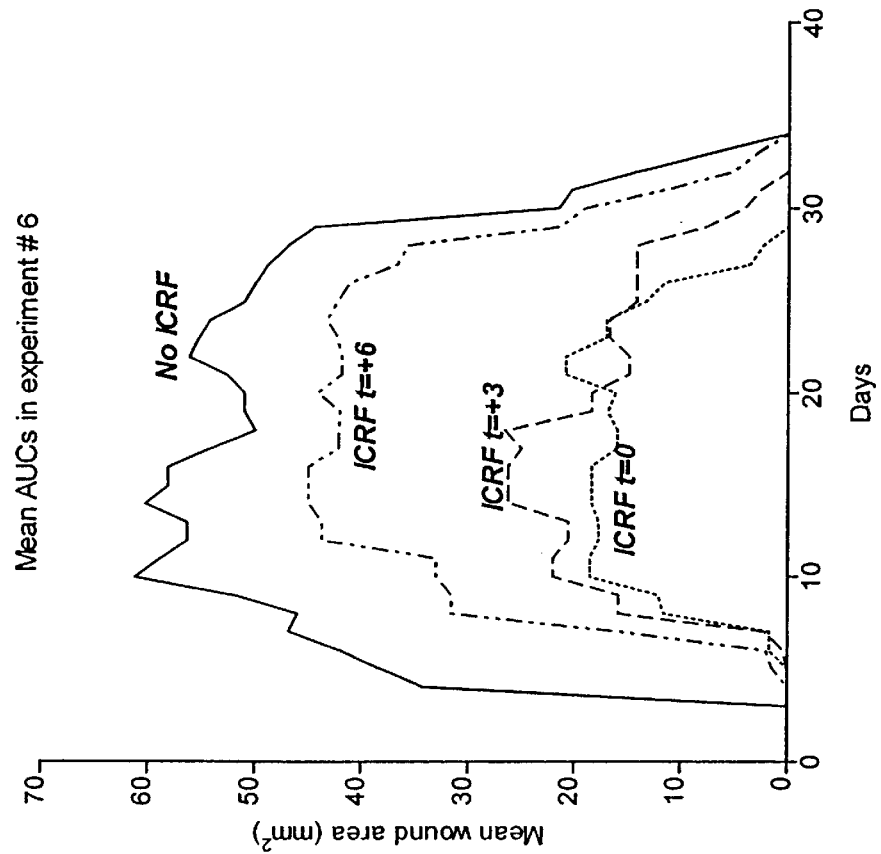
FIG. 5 shows the results from Example 6

ICRF-187 was administered at the same time as daunorubicin, 3 hours after, and 6 hours after, respectively. Saline served as control. The dose of daunorubicin was 3 mg/kg so and ICRF-187 was administered IP in a 250 mg/kg solution. Twenty-eight mice were used. The results are depicted in data sheet #6 and the mean AUCs are shown graphically in FIG. 5.

Data sheet for Example 6

| Gr. | Treatment | $N_w/N_G$ | Mean AUC ($mm^2$ × days) | Mean $TTW_w$ ± SEM (days) | Mean $DW_w$ ± SEM (days) |
|---|---|---|---|---|---|
| 1 | Daunorubicin 3 mg/kg sc + Saline IP | 7/7 100% | 1398 | 5.0 ± 0.4 | 27.4 ± 0.5 |
| 2 | Daunorubicin 3 mg/kg sc + ICRF-187 250 mg/kg IP | 7/7 100% | 326 | 7.7 ± 0.5 | 19.6 ± 0.7 |
| 3 | Daunorubicin 3 mg/kg sc + ICRF-187 250 mg/kg IP 3 hours after daunorubicin | 3/7 43% | 421 | 7.0 ± 0.6 | 21.0 ± 4.0 |
| 4 | Daunorubicin 3 mg/kg sc + ICRF-187 250 mg/kg IP 6 hours after daunorubicin | 7/7 100% | 926 | 6.7 ± 0.6 | 24.9 ± 0.8 |

The changes in AUCs reflected effect of ICRF-187 treatment when administered at the same time as daunorubicin as well as after 3 hours. Thus, the AUC was reduced with 77% at t=0 (p<0.05) and 70% at t=+3 hours (p<0.05). However, a 6 hours delay in ICRF-187 administration resulted in a statistically non-significant 34% reduction. Irrespective of administration time, treatment with ICRF-187 resulted in shorter duration of wounds (p<0.05).

Example 7

The Effect of Intralesional ICRF-187

100 mg/kg ICRF-187 was injected into the subcutaneous papule produced by injected daunorubicin. This treatment was compared to intralesional saline control, IP saline control, and IP treatment with ICRF-187. There were 9 mice in each group and no treatment-related deaths.

Data sheet for Example 7

| Gr. | Treatment | $N_w/N_G$ | Mean AUC ($mm^2 \times$ days) | Mean $TTW_w \pm$ SEM (days) | Mean $DW_w \pm$ SEM (days) |
|---|---|---|---|---|---|
| 1 | Daunorubicin 3 mg/kg sc + saline IP | 9/9 100% | 1144 | 6.0 ± 0.3 | 26.9 ± 0.7 |
| 2 | Daunorubicin 3 mg/kg sc + 0.05 ml saline IL | 9/9 100% | 1290 | 6.2 ± 0.3 | 24.4 ± 0.6 |
| 3 | Daunorubicin 3 mg/kg sc + 0.05 ml ICRF-187 100 mg/kg IL | 7/9 78% | 403 | 6.9 ± 1.6 | 19.4 ± 2.3 |
| 4 | Daunorubicin 3 mg/kg sc + ICRF-187 250 mg/kg IP | 8/9 89% | 562 | 9.6 ± 0.7 | 19.0 ± 0.9 |

IP treatment with ICRF-187 resulted in a reduction of the AUC with 51% (p<0.05). Local (intralesional) treatment with saline did not result in reduction in the AUC, and thus did not bring about any dilution effect. Furthermore, intralesional treatment with ICRF-187 produced a similar or even slightly more pronounced reduction in the AUC as obtained by the IP treatment. The time to wound was longer in the IP ICRF-187 treated group (p<0.05), and the reductions in wound duration with IP or IL ICRF-187 were statistically significant.

Example 8
Experiments with Epirubicin

In Example 8 a total of 28 mice were treated with epirubicin 4 mg/kg sc. Saline IP served as control, whereas treatment consisted of ICRF-187 125, 250 or 375 mg/kg IP, respectively. The results are presented in data sheet for Example 8:

Data sheet for Example 8

| Gr. | Treatment | $N_w/N_G$ | Mean AUC ($mm^2 \times$ days) | Mean $TTW_w \pm$ SEM (days) | Mean $DW_w \pm$ SEM (days) |
|---|---|---|---|---|---|
| 1 | Epirubicin 4 mg/kg sc + Saline IP | 4/7 57% | 195 | 9.3 ± 1.6 | 15.8 ± 2.5 |
| 2 | Epirubicin 4 mg/kg sc + ICRF-187 125 mg/kg IP | 2/7 29% | 147 | 5.5 ± 0.5 | 18.5 ± 0.5 |
| 3 | Epirubicin 4 mg/kg sc + ICRF-187 250 mg/kg IP | 2/7 29% | 134 | 5.0 | 19.5 ± 0.5 |
| 4 | Epirubicin 4 mg/kg sc + ICRF-187 375 mg/kg IP | 1/7 14% | 101 | 5.0 | 18.0 |

There were no statistically significant differences in AUCs of the four groups. However, when both AUCs and ulcer rates are taken in account, there was a trend towards a dose-dependent beneficial effect of treatment with ICRF-187. Statistical analysis of differences in duration of wounds or time to wounds is not meaningful.

It appears that the dose of epirubicin in Example 8 was to low. Hence, the effect of a higher dose of epirubicin will be subject for further investigation. Likewise, the effect of the time of administration of ICRF-187 in relation to axtravasation of epirubicin has not yet been investigated.

Example 9
Experiments with Idarubicin

In Example 9, 54 mice received idarubicin sc in increasing concentrations from 0.05 mg/kg to 0.75 mg/kg. Half of the groups served a saline controls, whereas in the other half of the groups ICRF-187 250 mg/kg was administered IP at t=0. The results are outlined in the data sheet for Example 9. There were no deaths due to the treatment.

Data sheet for Example 9

| Gr. | Treatment | $N_w/N_G$ | Mean AUC ($mm^2 \times$ days) | Mean $TTW_w \pm$ SEM (days) | Mean $DW_w \pm$ SEM (days) |
|---|---|---|---|---|---|
| 1 | Idarubicin 0.05 mg/kg sc + Saline IP | 0/9 0% | 0 | — | — |
| 2 | Idarubicin 0.05 mg/kg sc + ICRF-187 250 mg/kg IP | 1/9 11% | 4 | 12.0 ± 0.0 | 13.0 ± 0.0 |
| 3 | Idarubicin 0.25 mg/kg sc + Saline IP | 4/9 44% | 51 | 5.5 ± 0.9 | 11.0 ± 4.4 |

-continued

Data sheet for Example 9

| Gr. | Treatment | $N_w/N_G$ | Mean AUC ($mm^2 \times$ days) | Mean $TTW_w \pm$ SEM (days) | Mean $DW_w \pm$ SEM (days) |
|---|---|---|---|---|---|
| 4 | Idarubicin 0.25 mg/kg sc + ICRF-187 250 mg/kg IP | 1/9 11% | 38 | 6.0 ± 0.0 | 20.0 ± 0.0 |
| 5 | Idarubicin 0.75 mg/kg sc + Saline IP | 9/9 100% | 420 | 14.6 ± 7.8 | 20.2 ± 0.8 |
| 6 | Idarubicin 0.75 mg/kg sc + ICRF-187 250 mg/kg IP | 2/9 22% | 44 | 8.0 ± 0.0 | 17.5 ± 0.5 |

Figure 6:
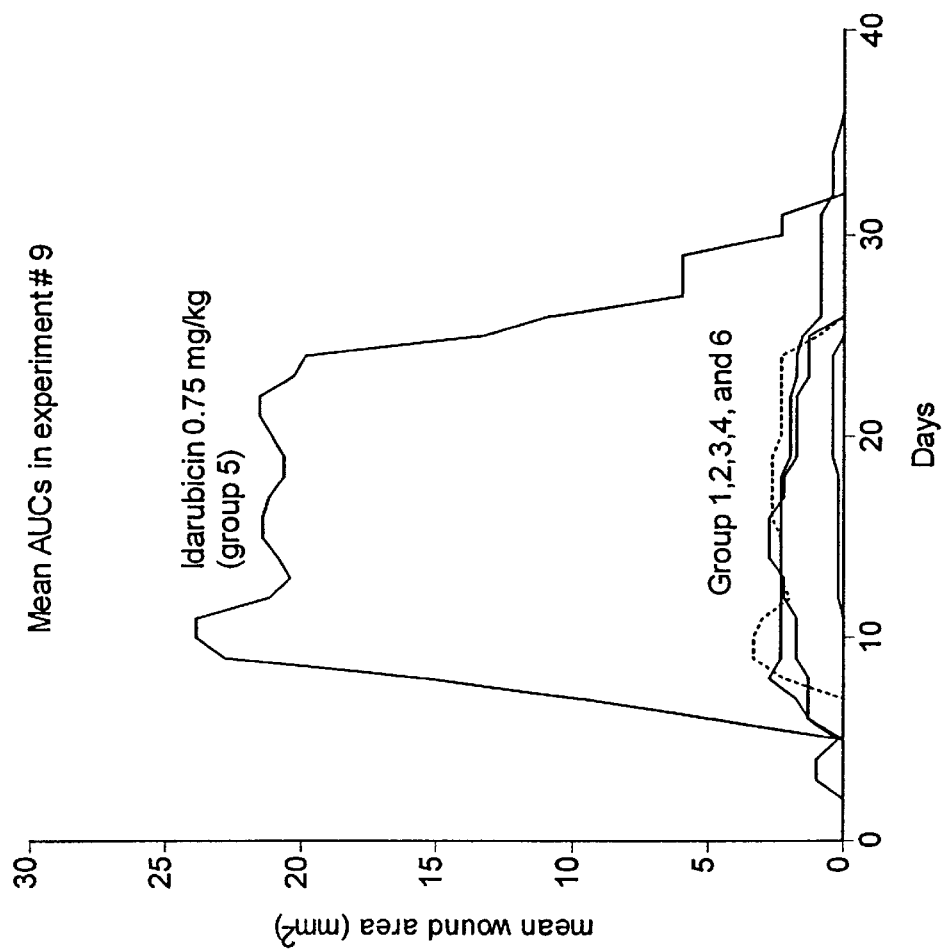
FIG. 6 shows the results from Example 9

At dose level 0.75 mg/kg, treatment with ICRF-187 resulted in a 90% reduction in the AUC compared to the saline control (p<0.05), see FIG. 6. Furthermore, the ulcer rates were reduced from 100% to 22% (p<0.05). The changes in AUCs between ICRF-187 treated groups and controls at lower doses of idarubicin were not statistically significant, and the numbers of wounds were too small for further statistical analysis. There was a dose dependent increase of mean AUCs in the control groups (p<0.05).

Example 10
Updated Experiments with Daunorubicin

Twenty-eight experiments have been conducted. Seven experiments (n=6, 7, 7, 9, 9, 9, and 9) with 3 mg/kg daunorubicin SC plus saline IP at t=0 and seven experiments (n=6, 7, 7, 9, 9, 8, and 9) with 3 mg/kg daunorubicin SC plus 250 mg/kg ICRF-187 IP at t=0 in two experiments (n=9 and 4) the ICRF-187 doses were 62,5 mg/kg and 375 mg/kg IP, respectively, in two (n=7 and 9) the dose was 125 mg/kg. ICRF-187 250 mg/kg was administered IV in one (n=9). ICRF-187 was administered as triple-treatment in three experiments: In one (n=8) the dose was 250 mg/kg IP at day 0, 1, and 2. In two others, ICRF-187 was injected at 0, 3 hours, and 6 hours after SC daunorubicin in a dose of 125 mg/kg (n=9) and 62,5 mg/kg (n=9), respectively.

Example 11
Updated Experiments with Doxorubicin

Twenty-eight experiments were performed. Six experiments (n=9, 9,18, 9, 9, and 7) with doxorubicin 2 or 3 mg/kg SC and saline IP at t=0, and six (n=9, 8, 16, 6, 9, and 9) with doxorubicin 2 or 3 mg/kg SC and ICRF-187 250 mg/kg IP at t=0. In two (n=9 and 7) the ICRF-187 dose was 125 mg/kg IP, in one (n=7) 375 mg/kg IP, and in one (n=9) 62,5 mg/kg IP. In a single experiment (n=9), doxorubicin 3 mg/kg SC was followed immediately by ICRF-187 250 mg/kg administered IV. ICRF-187 was administered as triple-treatment in three experiments: In one (n=9) the dose was 250 mg/kg IP at day 0, 1, and 2. In two others, ICRF-187 was injected at 0, 3 hours, and 6 hours after SC doxorubicin in a dose of 125 mg/kg (n=9) and 62,5 mg/kg (n=9), respectively. In one experiments (n=9) doxorubicin was administered SC in a dose of 1 mg/kg with saline IP, and in one (n=9) with 250 mg/kg ICRF-187 IP. ICRF-187 250 mg/kg was administered IP three (n=9 and 9) or six hours (n=9 and 9) after doxorubicin 2 or 3 mg/kg SC in four other experiments. Finally, premixing doxorubicin 3 mg/kg with either ICRF-187 250 mg/kg (n=9) or 30 mg/kg (n=9) for SC injection was performed in two experiments.

Results

Doxorubicin induced lesions were similar in sizes and duration, whether they were induced by SC injection of 2 or 3 mg/kg. Thus, these two dose levels are pooled (Table A). The inter-experimental variation in the mean AUC's in the seven experiments with daunorubicin 3 mg/kg SC plus saline IP was very small (p>0.05). Neither were the mean AUC's different in the seven experiments where daunorubicin 3 mg/kg SC were accompanied by ICRF-187 250 mg/kg IP at t=0 (FIG. 7). The same notable reproducibility was present in experiments with doxorubicin 2 or 3 mg/kg SC plus saline IP or plus ICRF-187 250 mg/kg IP. Furthermore, as the ICRF-187-treatment resulted in statistically significant reductions in the mean AUC in all the above mentioned experiments (individual Mann-Whitney tests all p<0.01), the individual data were pooled into two "basic" schedules with n=61 and 58 (doxorubicin), and n=56 and 55 mice (daunorubicin), respectively as depicted in Table A.

A single IP injection of ICRF-187 250 mg/kg administered immediately after a SC deposit of 3 mg/kg daunorubicin reduced the mean AUC by 70% (p<0.0001) (FIGS. 8 and 9). The fraction of mice with wounds was reduced from 96% to 78% (p=0.0041). In mice with detectable wounds, the mean time to wounds was delayed by 76% from 5.5 to 9.7 days (p<0.0001). Furthermore, ICRF-187 reduced the mean duration of wounds by 35% from 26.6 to 17.4 days (p<0.0001).

In the case of doxorubicin (FIGS. 8 and 10), the mean AUC after 2 or 3 mg/kg SC was reduced by 96% (p<0.0001) with ICRF-187 250 mg/kg IP at t=0. The fraction of mice with wounds was reduced from 77% to 14% (P<0.0001), the duration of wounds shortened with 28% (p=0.0035). There was no delay in the time to appearance of wounds.

In both daunorubicin and doxorubicin induced wounds, there was no statistically significant difference between the protection provided by IP injection of ICRF-187 compared to IV administration.

Reduction of the daunorubicin dose from 3 mg/kg to 1 mg/kg resulted in significantly smaller AUCs (p<0.0001) with no difference in frequency of wounds, time to, or duration of wounds. IP treatment with ICRF-187 also resulted in a statistically significant reduction in AUC (p<0.0001) at the low daunorubicin dose. Doxorubicin injected SC in doses below 2 mg/kg did not produce any wounds.

In daunorubicin induced lesions, the reduction in AUC decreased from 70% to 45% (p=0.0175), when the ICRF-187 dose was reduced from 250 mg/kg IP to 125 mg/kg. In contrast, the protection against doxorubicin injuries was evenly effective at all doses of ICRF-187.

Three or even six hours of delay in administration of ICRF-187 did not impair the degree of protection against doxorubicin lesions when compared to the effect obtained by treatment at t=0. Similarly, when ICRF-187 was administered 3 hours after the injection of daunorubicin, the protection was no different from the protection obtained by immediate ICRF-187 administration. However, the protection was lost if the delay was 6 hours. Treatment with ICRF-187 250 mg/kg IP three days in a row completely prevented both doxorubicin and daunorubicin induced lesions. Moreover, triple-treatment with ICRF-187 62,5 mg/kg or 125 mg/kg IP administered 0, 3 and 6 hours after injection of daunorubicin or doxorubicin resulted in at least the same degree of protection as a single injection of 250 mg/kg ICRF-187 IP.

The dose of ICRF-187 correlated inversely with the protection against wounds in the two experiments were ICRF-187 and doxorubicin were mixed before SC injection. Thus, SC injection of a mixture of ICRF-187 30 mg/kg and doxorubicin 3 mg/kg resulted in complete protection against wounds. However, the increment of the dose of ICRF-187 to 250 mg/kg in the same volume resulted in appearance of wounds in seven of nine treated mice.

FIG. 7 shows that the induction of wounds by SC daunorubicin and the protection from such lesions with IP ICRF-187 is highly reproducible.

The mean area under the curve (AUC) from 7 independent experiments with daunorubicin 3 mg/kg SC+/−ICRF-187 250 mg/kg IP at t=0. The inter-experimental variation was not statistically different in the treated (plus ICRF-187; p=>0.05, Student-Newmann-Kents test)) or the controls (no ICRF-187; p=>0.05). Treatment with ICRF-187 resulted in statistically lower mean AUCs (p<0.001) in all experiments. □=No ICRF-187; •=Plus ICRF-187; - - -=mean; bars=SEM FIG. 8 shows that the protection against daunorubicin induced lesions is more dose- and time-dependent than against injuries caused by SC doxororubicin. The marked protection obtained by triple-treatment with ICRF-187 is very surprising. The histograms compare the mean AUCs of different schedules of ICRF-187 after SC injection of 3 mg/kg daunorubicin (FIG. 8A), 0.75 mg/kg idarubicin (FIG. 8B), and 2 or 3 mg/kg doxorubicin, respectively (FIG. 8C). Mean AUC: Mean area under the curve (mm$^2$xdays); n: number of mice; bars: SEM.

Legends: Except for the bars representing saline, the legends depict the dose, route of administration, and timing of ICRF-187.

FIG. 9 shows that a single systemic injection of ICRF-187 significantly reduces the wounds induced by SC daunorubicin.

Left graph: Scatter plot showing the distribution of the AUCs of individual mice after 3 mg/kg daunorubicin SC followed by saline IP (O; n=56) or ICRF-187 250 mg/kg IP at t=0 (•;n=55). Horizontal lines indicate mean AUCs.

Right graph: Mean wound area vs time of the same data as in the left graph. The difference in AUCs is highly significant. Moreover, the curves reveal the delay in the appearance and the shorter duration of wounds DEX: dexrazoxane=ICRF-187; AUC: Area under the curve.

FIG. 10 shows that a single systemic injection of ICRF-187 significantly reduces the wounds induced by SC doxorubicin.

Left graph: Scatter plot showing the distribution of the AUCs of individual mice after 2 or 3 mg/kg doxorubicin SC followed by saline IP (O; n=56) or ICRF-187 250 mg/kg IP at t=0 (•;n=55). Horizontal lines indicate mean AUCs.

Right graph: Mean wound area vs time of the same data as in the left graph. The difference in AUCs is highly significant.

DEX: dexrazoxane=ICRF-187; AUC: Area under the curve.

Table A

Results of the treatment of SC daunorubicin, idarubicin, and doxorubicin induced wounds in mice. If nothing else is stated, the treatment (ICRF-187 or saline) were administered at t=0.

DEX: Dexrazoxane=ICRF-187; AUC: Mean area under the curve (mm$^2$xdays); FW: Fraction of mice with wounds (%); TTW: Mean time to appearance of wound (days); DW: Mean duration of wound (days); Brackets: Standard error of the mean, SEM; *: Pooled data (see Results for details); n: Number of mice

|  | Treatment | n | AUC | FW | TTW | DW |
| --- | --- | --- | --- | --- | --- | --- |
|  | Daunorubicin |  |  |  |  |  |
| 3 mg/kg SC | Saline IP | 56* | 1260 (± 72) | 96 | 5.5 (± 0.2) | 26.6 (± 0.3) |
| 3 mg/kg SC | DEX 250 mg/kg IP | 55* | 373 (± 48) | 78 | 9.7 (± 0.5) | 17.4 (± 0.6) |
| 3 mg/kg SC | DEX 62,5 mg/kg IP | 9 | 662 (± 223) | 89 | 8.1 (± 0.5) | 19.4 (± 1.3) |
| 3 mg/kg SC | DEX 125 mg/kg IP | 16* | 692 (± 115) | 88 | 8.4 (± 0.6) | 20.6 (± 0.8) |
| 3 mg/kg SC | DEX 375 mg/kg IP | 4 | 57 (± 57) | 25 | 4.0 (± 0.0) | 23.0 (± 0.0) |
| 3 mg/kg SC | DEX 62,5 mg/kg IP at t = 0, t = +3h, and t = +6h | 9 | 0 | 0 | — | — |
| 3 mg/kg SC | DEX 125 mg/kg IP at t = 0, t = +3h, and t = +6h | 9 | 112 (± 37) | 22 | 16.5 (± 0.5) | 18.0 (± 0.0) |
| 3 mg/kg SC | DEX 250 mg/kg IP day 0, 1, and 2 | 8 | 128 (± 34) | 75 | 17.7 (± 1.0) | 13.3 (± 1.2) |
| 3 mg/kg SC | DEX 250 mg/kg IP at t = +3h | 7 | 420 (± 206) | 43 | 7.0 (± 0.6) | 21.0 (± 4.0) |
| 3 mg/kg SC | DEX 250 mg/kg IP at t = +6h | 7 | 927 (± 163) | 100 | 6.7 (± 0.6) | 24.9 (± 0.8) |
| 3 mg/kg SC | DEX 250 mg/kg IV | 9 | 479 (± 141) | 67 | 9.2 (± 1.2) | 19.3 (± 1.3) |
| 1 mg/kg SC | Saline IP | 16* | 263 (± 56) | 88 | 6.9 (± 0.7) | 22.6 (± 1.1) |
| 1 mg/kg SC | DEX 250 mg/kg IP | 16* | 28 (± 22) | 13 | 10.5 (± 3.5) | 16.0 (± 4.0) |
|  | Idarubicin |  |  |  |  |  |
| 0.75 mg/kg SC | Saline IP | 18* | 308 (± 58) | 83 | 6.7 (± 0.4) | 21.2 (±0.7) |
| 0.75 mg/kg SC | DEX 250 mg/kg IP | 18* | 42 (± 19) | 28 | 10.2 (± .5) | 15.6 (± 2.7) |
| 0.05 mg/kg SC | Saline IP | 9 | 0 | 0 | — | — |
| 0.05 mg/kg SC | DEX 250 mg/kg IP | 9 | 4 (± 4) | 11 | 12.0 (± 0.0) | 13.0 (± 0.0) |

-continued

| | Treatment | n | AUC | FW | TTW | DW |
|---|---|---|---|---|---|---|
| 0.25 mg/kg SC | Saline IP | 9 | 51 (± 22) | 44 | 5.5 (± 0.9) | 24.8 (± 1.4) |
| 0.25 mg/kg SC | DEX 250 mg/kg IP | 9 | 38 (± 38) | 11 | 6.0 (± 0.0) | 20.0 (± 0.0) |
| 1.50 mg/kg SC | Saline IP | 9 | 353 (± 97) | 78 | 7.1 (± 0.6) | 19.4 (± 2.0) |
| 1.50 mg/kg SC | DEX 250 mg/kg IP | 8 | 183 (± 54) | 75 | 7.7 (± 0.2) | 17.8 (± 0.9) |
| | Doxorubicin | | | | | |
| 2 and 3 mg/kg SC | Saline IP | 61* | 467 (± 61) | 77 | 9.3 (± 0.5) | 20.5 (± 0.7) |
| 2 and 3 mg/kg SC | DEX 250 mg/kg IP | 58* | 17 (± 7) | 14 | 8.6 (± 1.8) | 14.8 (± 1.9) |
| 3 mg/kg SC | DEX 62.5 mg/kg IP | 9 | 21 (± 14) | 22 | 12.0 (± 2.0) | 17.5 (± 1.5) |
| 2 and 3 mg/kg SC | DEX 125 mg/kg IP | 16* | 32 (± 23) | 13 | 10.2 (± 1.2) | 17.0 (± 0.9) |
| 2 mg/kg SC | DEX 375 mg/kg IP | 7 | 0 | 0 | — | — |
| 3 mg/kg SC | DEX 62,5 mg/kg IP at t = 0, +3, and +6h | 9 | 0 | 0 | — | — |
| 3 mg/kg SC | DEX 125 mg/kg IP at t = 0, +3, and +6h | 9 | 34 (± 23) | 22 | 14.0 (± 1.0) | 14.0 (± 2.0) |
| 3 mg/kg SC | DEX 250 mg/kg IP on day 0, 1, and 2 | 9 | 0 | 0 | — | — |
| 2 and 3 mg/kg SC | DEX 250 mg/kg IP at t = +3h | 18* | 62 (± 37) | 28 | 7.2 (± 1.0) | 19.0 (± 1.5) |
| 2 and 3 mg/kg SC | DEX 250 mg/kg IP at t +6h | 18* | 77 (± 20) | 50 | 9.3 (± 1.1) | 18.2 (± 0.8) |
| 3 mg/kg SC | DEX mg/kg IP 250 IV | 9 | 17 (± 11) | 22 | 10.5 (± 0.5) | 12.0 (± 1.0) |
| 3 mg/kg SC | Mixed with DEX 30 mg/kg | 9 | 0 | 0 | — | — |
| 3 mg/kg SC | Mixed with DEX 250 mg/kg | 9 | 169 (± 47) | 78 | 6.6 (± 2.0) | 18.3 (± 1.6) |
| 1 mg/kg SC | Saline IP | 9 | 0 | 0 | — | — |
| 1 mg/kg SC | DEX 250 mg/kg IP | 9 | 0 | 0 | — | — |

Example 12
Pilot Studies on Swine

A danish porker weighting approximately 30 kg was used. The animals were fully anesthesized and artificially ventilated during SC injection of 1 ml of anthracycline. I one experiment (n=2) a wound appeared after 3 mg doxorubicin SC in the swine not receiving ICRF-187, whereas the swine treated with 25 mg/kg ICRF-187 IV at t=0 did not develope an ulcer. In the second experiment (n=3), no wound appeared after 1 ml daunorubicin SC in a swine treated with 25 mg/kg ICRF-187 IV daily for three days, a small wound appeared in the swine treated with 50 mg/kg IV at t=0, and a large wound appeared in the untreated swine.

In summary, the experiments performed on swine confirmed results from our murine experiments, i.e. ICRF-187 protects against lesions induced by SC anthracyclines in a schedule-dependent manner.

Example 13
Clinical Results in a Patient

A female patient in whom 149 mg of doxorubicin was infused subcutaneously instead of into a port-a-cath has been treated according to the present invention.

Treatment with ICRF-187 was initiated 2 h 30 m after the extravasation with a dose of 1000 mg/m$^2$ day 1, 1000 mg/$^2$ day 2, and 500 mg/$^2$ on day 3 of the ICRF-187. In the following weeks she experienced no side effects from the treatment. Weekly evaluation by a clinical oncologist and a plastic surgeon as well as with ultrasound revealed a subcutaneous mass of approximately 3×4 cm that did not change in size during the evaluation period of 30 days after the incident. No ulcer or signs of skin-necrosis developed in spite of the massive dose of doxorubicin. The patient continued chemotherapy with a delay of only one week and without surgical intervention.

Reference List
1. Froelich-Ammon S J, Osheroff N. Topoisomerase poisons: Harnessing the dark side of enzyme mechanism. J Biol Chem 1995;270:21429–32.
2. Chen A Y, Liu L F. DNA topoisomerases: Essential enzymes and lethal targets. Annu Rev Pharma Toxicol 1994;34:191–218.
3. Jensen P B, Sørensen B S, Sehested M, Grue P, Demant E J F, Hansen H H. Targeting the cytotoxicity of topoisomerase II directed epipodophyllotoxins to tumor cells in acidic environments. Cancer Res. 1994;54:2959–63.
4. Sehested M, Jensen P B. Mapping of DNA topoisomerase II poisons (etoposide, clerocidin) and catalytic inhibitors (aclarubicin, ICRF-187) to four distinct steps in the topoisomerase II catalytic cycle. Biochem. Pharmacol. 1996;51:879–86.
5. ½Sørensen B S, Sinding J, Andersen A H, Alsner J, Jensen P B, Westergaard O. Mode of action of topoisomerase II targeting agents at a specific DNA sequence: Uncoupling the DNA binding, cleavage and religation events. J Mol Biol 1992;228:778–86.

6. Tanabe K, Ikegami Y, Ishida R, Andoh T. Inhibition of topoisomerase II by antitumor agents bis(2,6-dioxopiperazine) derivatives. Cancer Res 1991;51:4903–8.
7. Berger J M, Gamblin S J, Harrison S C, Wang J C. Structure and mechanism of DNA topoisomerase II. Nature 1996;379:225–32.
8. Roca J, Ishida R, Berger J M, Andoh T, Wang J C. Antitumor bisdioxopiperazines inhibit yeast DNA topoisomerase II by trapping the enzyme in the form of a closed protein clamp. Proc Natl Acad Sci USA 1994;91:1781–5.
9. Roca J, Berger J M, Harrison S C, Wang J C. DNA transport by a type II topoisomerase: Direct evidence for a two-gate mechanism. Proc Natl Acad Sci USA 1996;93:4057–62.
10. Von Hoff D D, Layard M V, Basa P, et al. Risk factors for doxorubicin-induced congestive heart failure. Ann. Intern. Med. 1979;91:710–7.
11. Von Hoff D D, Layard. Risk factors for development of daunorubicin-cardiotoxicity. Cancer Treat. Rep. 1981;65 ((suppl 4)):19–23.
12. Hasinoff B B. The iron(III) and copper(II) complexes of adriamycin promote the hydrolysis of the cardioprotective agent ICRF-187 ((+)-1,2-bis(3,5-dioxopiperazinyl-1-yl) propane). Agents and Actions 1990;29:374–81.
13. Sehested M, Wessel I, Jensen L H, Holm B, Olivieri R S, Kenwrick S, Creighton A M, Nitiss J L, Jensen P B. Chinese hamster ovary cells resistant to the topoisomerase II catalytic inhibitor ICRF-159; a Tyr49Phe mutation confers high level resistance to bisdioxopiperazines. Cancer Res. 1998;58:1460–8.
14. Wessel I, Jensen L H, Jensen P B, Faick J, Roerth M, Nitiss J L, Sehested M. Human small cell lung cancer NYH cells selected for resistance to the bisdioxopiperazine topoisomerase II (topoII) catalytic inhiibitor ICRF-187 (NYH/187) demonstrate a functional Arg 162Gln mutation in the Walker A consensus ATP binding site of the a isoform. [Abstract] Proc. AACR 1998;39:375
15. Sørensen M, Sehested M, Jensen P B. pH-dependent regulation of camptothecin induced cytotoxicity and cleavable complex formation by the antimalarial agent chloroquin. Biochem. Pharmacol. 1997;54:373–80.
16. Ishida R, Miki T, Narita T, Yui R, Sato M, Utsumi K R, Tanabe K, Andoh T. Inhibition of intracellular topoisomerase II by antitumor bis(2,6-dioxopiperazine) derivatives: Mode of cell growth inhibition distinct from that of cleavable complex-forming type inhibitors. Cancer Res 1991;51:4909–16.
17. Roca J, Wang J C. DNA transport by a type II DNA topoisomerase: Evidence in favor of a two-gate mechanism. Cell 1994;77:609–16.
18. Sehested M, Jensen P B, Sørensen B S, Holm B, Friche E, Demant E J F. Antagonistic effect of the cardioprotector (+)-1,2,-bis(3-5-dioxopiperazinyl-1-yl)propane (ICRF-187) on DNA breaks and cytotoxicity induced by the topoisomerase II directed drugs daunorubicin and etoposide (VP-16). Biochem. Pharmacol. 1993;46:389–93.
19. Loth T S, Eversmann W W, Jr. Treatment methods for extravasations of chemotherapeutic agents: a comparative study. J. Hand Surg. Am. 1986;11 (3):388–96.
20. Sonneveld P, Wassenaar H A, Nooter K. Long persistence of doxorubicin in human skin after extravasation. Cancer Treat. Rep. 1984;68(6):895–6.
21. Banerjee A. Cancer chemotherapy agent-induced perivenous extravasation injuries. Postgrad. Med. 1987;635–9.
22. Dorr R T, Alberts D S, Stone A. Cold protection and heat enhancement of doxorubicin skin toxicity in the mouse. Cancer Treat. Rep. 1985;69(4):431–7.
23. Dorr R T, Alberts D S, Chen H S. The limited role of corticosteroids in ameliorating experimental doxorubicin skin toxicity in the mouse. Cancer Chemother. Pharmacol. 1980;5:17
24. Bartowski D L, Daniels J R. Use of sodium bicarbonate as a means of ameliorating doxorubicin-induced dermal necrosis in rat. Cancer Chemother. Pharmacol. 1981;4:179
25. Disa J J, Chang R R, Mucci S J, Goldberg N H. Prevention of adriamycin-induced full-thickness skin loss using hyaluronidase infiltration. Plast. Reconstr. Surg. 1998;101(2):370–4.
26. Dorr R T, Alberts D S. Modulation of experimental doxorubicin skin toxicity by beta-adrenergic compounds. Cancer Res. 1981;41(6):2428–32.
27. Dorr R T, Alberts D S. Failure of DMSO and vitamin E to prevent doxorubicin skin ulceration in the mouse. Cancer Treat. Rep. 1983;67(5):499–501.
28. Soble M, Dorr R T, Plezia P, Breckenridge S. Dose-dependent skin ulcers in mice treated with DNA binding antitumor antibiotics. Cancer Chemother. Pharmacol. 1987;20:33–6.
29. Bekerecioglu M, Kutluhan A, Demirtas I, Karaayvaz M. Prevention of adriamycin-induced skin necrosis with various free radical scavengers. J. Surg. Res. 1998;75(1):61–5.
30. Averbuch S D, Gaudiano G, Koch T H, Bachur N R. Doxorubicin-induced skin necrosis in the swine model: protection with a novel radical dimer. J. Clin. Oncol. 1986;4(1):88–94.
31. Dahlstrom K K, Chenoufi H L, Daugaard S. Fluorescence microscopic demonstration and demarcation of doxorubicin extravasation. Experimental and clinical studies. Cancer 1990;65(8):1722–6.
32. Rudolph R, Suzuki M, Luce J K. Experimental skin necrosis produced by adriamycin. Cancer Treat. Rep. 1979;63(4):529–37.
33. Bleicher J N, Haynes W, Massop D W, Daneff R M. The delineation of adriamycin extravasation using fluorescence microscopy. Plast. Reconstr. Surg. 1984;74(1):114–6.
34. Luedke D W, Kennedy P S, Rietschel R L. Histopathogenesis of skin and subcutaneous injury induced by adriamycin. Plast. Reconstr. Surg. 1979;63(4):463–5.
35. Brothers T E, Von Moll L K, Niederhuber J E, Roberts J A, Walker-Andrews S, Ensminger W D. Experience with subcutaneous infusion ports in three hundred patients. Surg Gynecol Obstet 1988;166:295
36. European Communities Council B 86 A.D.; 86/609/EEC.
37. The Council of Europe Convention S 1986;
38. Svendsen P. Svendsen P and Hau J, editors. Handbook of Laboratory Animal Science. 1 ed. CRC Press Inc; 1994. 332p.

What is claimed is:

1. A method for preventing or treating local tissue damage due to accidental extravasation of a cytotoxic topoisomerase II poison in a patient receiving treatment with the topoisomerase II poison, comprising administration of a topo II catalytic inhibitor to the patient in need thereof,
   where said topo II catalytic inhibitor is a bisdioxopiperazine.

2. A method according to claim 1 wherein the bisdioxopiperazine ICRF-187, (dexrazoxane).

3. A method according to claim 1 wherein the administration of the topo II catalytic inhibitor is by local administration to the tissue affected by the extravasation of the topoisomerase II poison.

4. A method according to claim 1 wherein the administration of the topo II catalytic inhibitor is by systemic administration to the tissue affected by the extravasation of the topoisomerase II poison.

5. A method according to claim 1 wherein the topoisomerase II poison is selected from the group consisting of etoposide, etoposide phosphate, teniposide, mitoxantrone, and m-AMSA.

6. A method according to claim 1 wherein the topo II catalytic inhibitor is administered after the treatment with the topoisomerase II poison.

7. A method according to claim 1 wherein the topo II catalytic inhibitor is administered after treatment with the topoisomerase II poison and while the tissue contains topoisomerase II poison or its active metabolites.

8. A method according to claim 3 wherein the topo II inhibitor is administered after the occurrence of accidental extravasation of said topoisomerase II poison.

9. A method according to claim 8 wherein the topo II inhibitor is administered after first occurrence of pain, erythema or swelling due to accidental extravasation of said topoisomerase II poison.

10. A method according to claim 7 wherein the topo II inhibitor is administered more than 24 hours after administration of the topoisomerase II poison.

11. A method according to claim 7 wherein the topo II inhibitor is first administered more than 24 hours after administration of the topoisomerase II poison.

12. A method according to claim 1 wherein the topo II catalytic inhibitor is administered substantially concomitantly with the administration of the topoisomerase II poison.

13. A method according to claim 1, wherein the topo II catalytic inhibitor is administered in the period within 3 weeks after the administration of the topo II poison.

14. A method according to claim 1, wherein the topo II catalytic inhibitor is administered in the period within 18 hours after the administration of the topo II poison.

15. A method according to claim 1, wherein the topo II catalytic inhibitor is administered with at least 2 repeated dosages.

16. A method according to claim 15, wherein the repeated dosages are administered with an interval of 1 to 3 days from the first dosage.

17. A method according to claim 15, wherein the repeated dosages are administered with an interval of at the most 24 hours from the first dosage of the topo II catalytic inhibitor.

18. A method according to claim 1, wherein the II catalytic inhibitor is administered with at least 3 repeated dosages.

19. A mehtod according to claim 18, wherein the topo II catalytic inhibitor is administered with at least 4 repeated dosages.

20. A method according to claim 1, wherein the topo II catalytic inhibitor is administered within 12 hours of recognition or suspicion of extravasation of the topoisomerase II poison.

21. A method according to claim 1, wherein the topo II catalytic inhibitor is administered within 12 hours of administration of the topoisomerase II poison.

22. A method according to claim 1, wherein the topoisomerase II poison is an anthracycline.

23. A method according to claim 22 wherein the topoisomerase II poison is selected from the group consisting of daunorubicin, doxorubicin, idarubicin, and epirubicin.

24. A method according to claim 1, wherein the topoisomerase II poison is daunorubicin.

25. A method according to claim 1, wherein the topoisomerase II poison is doxorubicin.

26. A method according to claim 1, wherein the topoisomerase II poison is idarubicin.

27. A method according to claim 1, wherein the topoisomerase II poison is epirubicin.

28. A method according to claim 1 wherein the topo II inhibitor is administered in an amount sufficient to be present in the tissue to be prevented from or treated for tissue damage.

29. A method according to claim 1, wherein the topo II catalytic inhibitor is administered within 6 hours of administration of the topoisomerase II poison.

30. A method according to claim 1, wherein the topo II catalytic inhibitor is administered within 4 hours of administration of the topoisomerase II poison.

31. A method according to claim 1, wherein the topo II catalytic inhibitor is administered within 2 hours of administration of the topoisomerase II poison.

* * * * *